United States Patent [19]

De Luca et al.

[11] Patent Number: 5,814,520
[45] Date of Patent: Sep. 29, 1998

[54] TRYPTAMINE PRODUCING TRYPTOPHAN DECARBOXYLASE GENE OF PLANT ORIGIN

[75] Inventors: Vincenzo De Luca, Rivière des Prairies; Normand Brisson, Montreal; Wolfgang Gebhard Walter Kurz, Saskatoon, all of Canada

[73] Assignee: National Research Council Canada, Ottawa, Canada

[21] Appl. No.: 426,163

[22] Filed: Apr. 20, 1995

Related U.S. Application Data

[63] Continuation of Ser. No. 82,418, Jun. 28, 1993, abandoned, which is a continuation-in-part of Ser. No. 758,493, Sep. 5, 1991, abandoned, which is a continuation of Ser. No. 314,879, Feb. 24, 1989, abandoned.

[51] Int. Cl.$^6$ .............................. C12N 5/04; C12N 1/21; C12N 15/60
[52] U.S. Cl. ................. 435/419; 435/252.3; 435/252.33; 536/23.2; 536/24.31
[58] Field of Search ................................ 435/252, 252.3, 435/252.33, 240.1, 108, 183, 419; 536/23.6, 23.2, 24.1

[56] References Cited

FOREIGN PATENT DOCUMENTS

WO90/10073  9/1990  WIPO.

OTHER PUBLICATIONS

Noe et al 1984 Plant Mol. Biol. vol. 3 281–288.
Maniatis et al 1982 Molecular Cloninic, Sect pp. 212–246.
De Luca et al. 1989 PNAS 86:2582–2586.
Broom et al. PNAS 1978 (75):2746–2749.
Albert, V.R., et al., "A Single Gene Codes for Aromatic L–Amino Acid Decarboxylase in Both Neuronal and Non–Neuronal Tissues," *J. Biol. Chem.*, 262:9404–9411 (1987).
Broom, et al., *Proc. Natl. Acad. Sci. USA*, 75: 2746–2749 (1978).
Chavadez, S., et al., "Production of Transgenic Plants which Accumulate Tryptamine Through Expression of Tryptophan Decarboxylase," *International Society for Plant Molecular Biology, Third International Congress*, Abstract 1098 (1991).
De Luca, et al., "Molecular Cloning and Analysis of cDNA Encoding a Plant Tryptophan Decarboxylase: Comparison with Animal dopa Decarboxylases," *Proc. Natl. Acad. Sci. USA*, 86: 2552–2556 (1989).
Eveleth, D.D., et al., "Sequence and Structure of the dopa Decarboxylase Gene of *Drosophila*: Evidence for Novel RNA Splicing Variants," *EMBO J.*, 5:2663–2672 (1986).
Facchini, P.J., and V. De Luca, "Differential and Tissue–Specific Expression of a Gene Family for Tyrosine/Dopa Decarboxylase in Opium Poppy," *J. Biol. Chem.*, 269:26684–26690 (1994).
Fecker, L., et al., "Expression of a Bacterial Lysine Decarboxylase Gene in Tobacco," *International Society for Plant Molecular Biology, Third International Congress*, Abstract 1092 (1991).
Joh, T.H., et al., "Molecular Biology of Aromatic L–Amino Acid Decarboxylase and B–Hydroxylase," *Progress in Catecholamine Research, Part a: Basic Aspects And Peripheral Mechanisms*, pp. 29–34 (1988).
Maniatis, et al., *Molecular Cloning*, pp. 212–246 (1982).
Noe, W., et al., "Tryptophan Decarboxylase from *Catharanthus roseus* Cell Suspension Cultures: Purification, Molecular and Kinetic Data of the Homogenous Protein," *Plant Mol. Biol.* vol. 3, pp. 281–288 (1984).
Songstad, D.D., et al., "High Levels of Trytamine Accumulation Accumulation in Transgenic Tobacco Expressing Tryptophan Decarboxylase," *Plant Physiol.*, 94:1410–1413 (1990).

*Primary Examiner*—Nancy T. Vogel
*Attorney, Agent, or Firm*—Quarles & Brady

[57] ABSTRACT

In accordance with the present invention, there is provided an isolated and purified DNA fragment comprising a DNA sequence encoding a plant decarboxylase. Preferably, the DNA sequence encodes a plant tryptophan decarboxylase, more preferably from *Catharanthus roseus*. A 1747 bp cDNA clone was isolated by antibody screening of a cDNA expression library produced from poly A$^+$ RNA found in developing seedlings of *C. roseus*. The invention also includes DNA sequences encoding a plant tryptophan decarboxylase which are synthetically produced to correspond substantially to the isolated and purified DNA sequence encoding the same enzyme. The nucleotide sequence of the synthetic DNA sequence is determined on the basis of codon degeneracy.

6 Claims, 13 Drawing Sheets

```
  1       CTCTCTCTCTCTCTCTCTAAGACTTTCTCTCTCTACACATACACCTAC asn  val  ala  met  ser  asn  ser  pro  val  glu  phe
  91      AAT  GTA  GCC  ATG  TCC  AAT  TCT  CCA  GTT  GGA  GAA  TTT arg  met  val  asp  phe  ile  ala  asp  tyr  tyr  lys  asn
 166      CGT  ATG  GTA  GAT  TTC  ATA  GCC  GAT  TAT  TAC  AAA  AAT tyr  leu  arg  lys  arg  ile  pro  glu  thr  ala  pro  tyr
 241      TAT  CTC  CGA  AAA  CGT  ATC  CCC  GAA  ACC  GCT  CCT  TAC lys  asp  ile  ile  pro  gly  met  thr  asn  trp  met  ser
 316      AAG  GAT  ATT  ATC  CCA  GGA  ATG  ACA  AAT  TGG  ATG  AGC ala  ala  phe  leu  gly  glu  met  leu  ser  thr  ala  leu
 391      GCT  GCC  TTT  TTA  GGA  GAA  ATG  TTG  TCT  ACT  GCC  CTA thr  glu  leu  glu  met  ile  val  met  asp  trp  leu  ala
 466      ACC  GAA  TTA  GAA  ATG  ATT  GTT  ATG  GAT  TGG  TTG  GCT thr  gly  gly  gly  val  ile  gln  asn  thr  thr  ser  glu
 541      ACC  GGT  GGC  GGC  GTC  ATC  CAA  AAC  ACC  ACT  AGC  GAG leu  glu  lys  leu  gly  pro  asp  ser  ile  gly  lys  leu
 616      CTG  GAG  AAG  CTC  GGT  CCC  GAT  AGT  ATT  GGA  AAA  CTT lys  thr  cys  lys  leu  ala  gly  ile  tyr  pro  asn  asn
 691      AAA  ACT  TGC  AAA  TTG  GCG  GGA  ATT  TAT  CCG  AAT  AAT ile  ser  pro  gln  val  leu  arg  lys  met  val  glu  asp
 766      ATC  TCA  CCT  CAA  GTT  CTA  CGA  AAA  ATG  GTC  GAG  GAT thr  leu  gly  thr  thr  ser  thr  thr  ala  thr  asp  pro
 841      ACC  CTG  GGT  ACC  ACC  TCG  ACC  ACG  GCT  ACC  GAT  CCT trp  ile  his  val  asp  ala  ala  tyr  ala  gly  ser  ala
 916      TGG  ATC  CAC  GTG  GAT  GCT  GCT  TAT  GCG  GGA  AGC  GCC glu  arg  val  asp  ser  leu  ser  leu  ser  pro  his  lys
 991      GAA  CGA  GTT  GAC  TCA  CTG  AGT  CTG  AGT  CCA  CAC  AAA lys  gln  pro  his  leu  leu  leu  arg  ala  leu  thr  thr
1066      AAG  CAA  CCA  CAT  TTG  TTA  CTA  AGG  GCA  CTC  ACT  ACG lys  val  val  asp  phe  lys  asn  trp  gln  ile  ala  thr
1141      AAA  GTT  GTG  GAC  TTC  AAA  AAT  TGG  CAA  ATC  GCA  ACG arg  ser  tyr  gly  val  val  asn  leu  gln  ser  his  ile
1216      CGT  AGC  TAT  GGA  GTT  GTT  AAT  TTA  CAG  AGT  CAT  ATT val  arg  ser  asp  ser  arg  phe  glu  ile  val  val  pro
1291      GTT  AGA  TCA  GAC  TCC  AGA  TTC  GAA  ATT  GTG  GTA  CCG val  ser  ser  leu  his  val  glu  glu  val  asn  lys  lys
1366      GTT  TCG  AGT  TTA  CAT  GTA  GAA  GAA  GTG  AAT  AAG  AAA thr  his  thr  ile  val  gly  gly  ile  tyr  met  leu  arg
1441      ACT  CAT  ACT  ATT  GTG  GGA  GGC  ATA  TAC  ATG  CTA  AGA arg  arg  val  trp  asp  leu  ile  gln  lys  leu  thr  asp
1516      CGC  CGT  GTT  TGG  GAT  TTG  ATT  CAA  AAA  TTA  ACC  GAT

1597      ATTTTTTTTTAAATTTTATATTTGCTGATTGTTTGAAGAGTTTAAAAA

1697      ATGTATTAATTATGACATGAGAATAAAATAGAATTTGTGTGTGCAAA
```

FIG 3A

```
                                      met  gly  ser  ile  asp  ser  thr
ACCAGAAAAAAGAAAAAAATA                 ATG  GGC  AGC  ATT  GAT  TCA  ACA lys  pro  leu  glu  ala  glu  glu  phe  arg  lys  gln  ala  his
AAG  CCA  CTT  GAA  GCT  GAG  GAA  TTC  CGA  AAA  CAA  GCC  CAT val  glu  thr  tyr  pro  val  leu  ser  glu  val  glu  pro  gly
GTG  GAA  ACA  TAT  CCG  GTC  CTT  AGC  GAA  GTC  GAA  CCT  GGA leu  pro  glu  pro  leu  asp  asp  ile  met  lys  asp  ile  gln
CTC  CCC  GAA  CCA  CTT  GAC  GAC  ATC  ATG  AAA  GAT  ATT  CAG pro  asn  phe  tyr  ala  phe  phe  pro  ala  thr  val  ser  ser
CCT  AAT  TTT  TAT  GCA  TTT  TTT  CCT  GCC  ACT  GTT  AGT  TCA asn  ser  val  gly  phe  thr  trp  val  ser  ser  pro  ala  ala
AAT  TCA  GTA  GGC  TTT  ACT  TGG  GTT  TCT  TCA  CCA  GCC  GCC gln  ile  leu  lys  leu  pro  lys  ser  phe  met  phe  ser  gly
CAG  ATC  CTT  AAA  CTC  CCC  AAA  TCT  TTC  ATG  TTT  TCA  GGT ser  ile  leu  cys  thr  ile  ile  ala  ala  arg  glu  arg  ala
TCC  ATT  CTT  TGT  ACA  ATC  ATT  GCC  GCC  CGG  GAA  AGG  GCC val  cys  tyr  gly  ser  asp  gln  thr  his  thr  met  phe  pro
GTC  TGT  TAC  GGA  TCC  GAT  CAA  ACC  CAT  ACC  ATG  TTC  CCC ile  arg  leu  ile  pro  thr  thr  val  glu  thr  asp  phe  gly
ATT  AGG  TTA  ATA  CCT  ACG  ACC  GTC  GAA  ACG  GAT  TTC  GGC asp  val  ala  ala  gly  tyr  val  pro  leu  phe  leu  cys  ala
GAC  GTG  GCG  GCC  GGA  TAT  GTA  CCG  CTG  TTT  TTA  TGC  GCT val  asp  ser  leu  ser  glu  ile  ala  asn  glu  phe  gly  ile
GTG  GAC  TCA  CTT  TCT  GAA  ATC  GCT  AAC  GAG  TTT  GGT  ATT cys  ile  cys  pro  glu  phe  arg  his  tyr  leu  asp  gly  ile
TGT  ATA  TGT  CCC  GAG  TTT  AGA  CAT  TAC  TTG  GAT  GGA  ATC trp  leu  leu  ala  tyr  leu  asp  cys  thr  cys  leu  trp  val
TGG  CTA  CTC  GCT  TAC  TTA  GAT  TGC  ACT  TGC  TTG  TGG  GTC asn  pro  glu  tyr  leu  lys  asn  lys  gln  ser  asp  leu  asp
AAT  CCT  GAG  TAT  TTA  AAA  AAT  AAA  CAG  AGT  GAT  TTA  GAC gly  arg  lys  phe  arg  ser  leu  lys  leu  trp  leu  ile  leu
GGA  CGA  AAA  TTT  CGG  TCG  CTG  AAA  CTT  TGG  CTC  ATT  TTA arg  ser  asp  val  ala  met  gly  lys  met  phe  glu  glu  trp
CGT  TCT  GAC  GTC  GCA  ATG  GGC  AAA  ATG  TTC  GAA  GAA  TGG arg  asn  phe  ser  leu  val  cys  phe  arg  leu  lys  pro  asp
AGA  AAC  TTT  TCT  CTT  GTT  TGT  TTT  AGA  TTA  AAA  CCT  GAC leu  leu  asp  met  leu  asn  ser  thr  gly  arg  val  try  met
CTT  TTG  GAC  ATG  CTT  AAC  TCG  ACG  GGA  CGA  GTT  TAT  ATG leu  ala  val  gly  ser  ser  leu  thr  glu  glu  his  his  val
CTG  GCT  GTT  GGC  TCA  TCG  CTA  ACT  GAA  GAA  CAT  CAT  GTA asp  leu  leu  lys  glu  ala  ter
GAT  TTG  CTC  AAA  GAA  GCT  TGA  TGAATAAGTAAGGGTTTTTTTTA
TAAAGTGATTTGTAAAGGTTTATTGTACTCAAACAATCATGCAATTAATTAT
AAAA
```

FIG 3B

```
AMD    VCEEFKCGSMLMPRMRWSLCSGGMF-GFAKGIGSRGLAKLQPAQVHAGQLRLLGHVAKGC
TDC    IANEFGIWIHVDAAYAGSACICPEFRHYLDGIERVDSLSLSPHKWLLAYLDCTCLWKQP
DDC1   VGNKHNLWIHVDAAYAGSAFICPEYRHLMKGIESADSFNFNPHKWMLVNFDCSAMLKDP
           300              310              320              330              340              350

AMD    QQGGRQLQCGSHLSEAQARGSVANSRLPSLANPLGRRFRALKVWITFRTLEAEGIRNHVA
TDC    HLLRALTTNPEYLKNKQSDLDKVVDFKNWQIATGRKFRSLKLWLILRSYGVVNLQSHIR
DDC1   SWVVNAFNVDPLYLKHDMQ--GSAPDYRHWQIPLGRRFRALKLWFVLRLYGVENLQAHIR
           360              370              380              390              400              410

AMD    KHIELAKQFEQLVLKDSRFEHVAPRALGLVCFRPKGD-----NEITTQLLQRLMDTKKV
TDC    SDVAMGKMFEEWVRSDSRFEIVVPERNFSLVCFRLKPDVSSLHVEEVNKKLLDMLNSTGRV
DDC1   RHCNFAKQFGDLCVADSRFELAAEINMGLVSFRLKGS-----NERNEALLKRINGRGHI
           420              430              440              450              460

AMD    YMTKTEHAGRQFLRFVVCGMDTKASDIDFAWQEIESQLTDLQADESLVARKSGNVGDLAH
TDC    YMTHIIVGGIYMLRLAVGSSLTEEHHVRRVWDLIQKLTDDLLKEA
DDC1   HLVPAKIKDVYGLRMAICSRFTQSEDMEYSWKEVSAAADEMEQEQ
           470              480              490              500              510

AMD    DFQIHLSTENATHEKSQ
```

FIG 4B

Leaf indole Glucosinolates (nmol/g fw)

Seed Indole Glucosinolates (µmol/g fw)

Seed Allyl Gulcosinolates (µmol/g fw)

TRYPTAMINE PRODUCING TRYPTOPHAN DECARBOXYLASE GENE OF PLANT ORIGIN

This is a continuation of application Ser. No. 08/082,418 filed Jun. 28, 1993, abandoned, which was a continuation-in-part of Ser. No. 07/758,493 filed Sep. 5, 1991, abandoned, which was a continuation of Ser. No. 07/314,879 filed on Feb. 24, 1989, now abandoned.

BACKGROUND OF THE INVENTION

Tryptophan decarboxylase (TDC; E.C. 4.1.1.27) catalyses the conversion of L-tryptophan to tryptamine. This enzyme has been detected in numerous plant systems and it has been suggested that its primary role is to supply possible precursors for auxin biosynthesis (Baxter, C. & Slaytor, M. (1972) Phytochemistry 11, 2763–2766; Gibson, R. A., Barret, G. & Wightman F. (1972) J. Exp. Bot. 23, pages 775–786; Gross, W. & Klapchek, S. (1979) Z. Pflanzenphysiol. 93, pages 359–363).

In the Gramineae, TDC catalyses the synthesis of precursors for the protoalkaloids which have considerable physiological activity in higher animals (Smith, T. A., (1977) Phytochemistry Vol. 16, pages 171–175). It is also known that tryptophan-derived tryptamines are also precursors of the tricyclic β-carboline alkaloids formed by condensation with a one- or two-carbon moiety (Slaytor, M., & McFarlane, I. J., (1968) Phytochemistry 7, pages 605–610).

Furthermore, in periwinkle (*Catharanthus roseus*), TDC produces tryptamine for biosynthesis of the commercially important antineoplastic monoterpenoid indole alkaloids, vinblastine and vincristine (De Luca, V., & Kurz, W. G. W. (1988), Cell Culture and Somatic Cell Genetics of Plants, Constabel, F. and Vasil, I. K., eds. Academic Press 5, pages 385–401).

The TDC from *Catharanthus roseus* has been purified to homogeneity. It occurs as a dimer consisting of 2 identical subunits of Mr 54,000 and it requires pyridoxal phosphate for activity (Noe, W., Mollenschott, C., & Berlin J. (1984) Plant Mol. Biol. 3, pages 281–288).

The enzyme possesses characteristics of plant aromatic decarboxylases which usually exhibit high substrate specificity. For example, TDC will decarboxylate L-tryptophan and 5-hydroxy-L-tryptophan but is inactive towards L-phenylalanine and L-tyrosine, while the tyrosine decarboxylases from *Syringa vulgaris* (Chapple, C. C. S., (1984) Ph.D. Thesis, University of Guelph, Guelph, Ontario, Canada), *Thalictrum rugosum* and *Escholtzia californica* (Marques, I. A., & Brodelius, P. (1988) Plant Physiol. 88, pages 52–55), accept L-tyrosine and L-dopa as substrates but not L-tryptophan or 5-hydroxy-L-tryptophan. The aromatic L-amino acid decarboxylases (dopa decarboxylase (DDC), ED 4.1.1.28) of *D. melanogaster* (Clark, W. C., Pass, P. S., Venkatararman, B., & Hodgetts, R. B. (1978) Mol. Gen. Genet. 162, pages 287–297; Eveleth, D. D., Gietz, R. D., Spencer C. A., Nargang, F. E., Hodgetts, R. B. & Marsh, J. L. (1986) Embo. J. 5, pages 2663–2672; Morgan B. A., Johnson, W. A. & Hirsh, J. (1986) Embo. J. 5, pages 3335–3342) and mammals (Albert, V. R., Allen, J. M., & Joh, T. H. (1987) J. Biol. Chem. 262, pages 9404–9411) have a broader substrate specificity with L-dopa, tyrosine, phenylalanine and possibly histidine also serving as substrates.

In animals, the role of aromatic L-amino acid decarboxylase is to produce the major neurotransmitters dopamine and serotonin and, in *D. melanogaster*, the DDC enzyme serves a second, inducible role, in the sclerotization of the insect cuticle (Christenson, J. G., Dairman, W. & Undenfriend, S. (1972) Proc. Natl. Acad. Sci. USA 69, pages 343–347; Lovenberg, W., Weissbach, W., & Undenfriend S. (1962) J. Biol. Chem. 237, pages 89–93; Yuwiler, A., Geller, E. & Eiduson, S. (1954) Arch. Biochem. Biophys. 80, pages 162–173; Brunet, P. (1980) Insect Biochem. 10, pages 467–500).

Glucosinolates are secondary products widely distributed throughout the family Cruciferae and while their biological function is not definitely known, defensive roles against pathogenic bacteria, fungi and insect herbivores have been suggested. In some commercially important Brassicas, the presence of glucosinolates is desirable as they provide the sharp taste of condiments, as well as the unique flavors and aromas associated with vegetables such as cabbage, broccoli, cauliflower and brussel sprouts.

On the other hand, glucosinolates are considered undesirable by-products when they are found in rapeseed protein meals after extraction of seeds for oil. In this case, the presence of glucosinolates significantly decrease the value of the meal as a feedstock since they can (i) be goiterogenic for livestock, (ii) affect weight gain and (iii) decrease the palatability of the meal. The high sulfur content of glucosinolates can also cause cattle to produce of f-flavored milk, and can taint the taste of meat, poultry and eggs. Therefore, the presence of considerable amounts of glucosinolates in rapeseed meals prevent their large scale use as an animal feed.

Intensive plant breeding programs have successfully reduced glucosinolate levels in Brassica oil seeds. Crosses made with the low glucosinolate Polish cultivar Boronowski produced "double low" commercial rapeseed cultivars, now known as canola, which contained no erucic acid and low levels of aliphatic glucosinolates. However, the levels of indole glucosinolates remained unchanged in these new cultivars.

In summary, it would appear highly desirable to be able to clone the cDNA sequence of tryptophan decarboxylase from *Catharanthus roseus*, thus, providing the development of the cDNA sequence in a plasmid vector capable of transforming cell lines that will produce the tryptophan decarboxylase enzyme.

If the tryptophan decarboxylase gene could be inserted into living organisms by transformation to produce tryptamine and related protoalkaloids, it could supplement a neurotransmitter deficiency or perhaps alter the spectrum of tryptophan-based chemicals normally produced by the plant.

SUMMARY OF THE INVENTION

In accordance with the present invention, there is provided an isolated and purified DNA fragment comprising a DNA sequence encoding a plant decarboxylase.

Preferably, the DNA sequence encodes a plant tryptophan decarboxylase, more preferably from *Catharanthus roseus*. A 1747 bp cDNA clone was isolated by antibody screening of a cDNA expression library produced from poly $A^+$ RNA found in developing seedlings of *C. roseus*.

The invention also includes DNA sequences encoding a plant tryptophan decarboxylase which are synthetically produced to correspond substantially to the isolated and purified DNA sequence encoding the same enzyme. The nucleotide sequence of the synthetic DNA sequence is determined on the basis of codon degeneracy.

Also within the scope of the present invention is a host cell having an extrachromasomal gene encoding a plant tryptophan decarboxylase, preferably a gene encoding a tryptophan decarboxylase from *C. roseus*. Preferred host cells include plant cells such as tobacco, canola and potato and bacterial cells such as *E. coli*.

The plant TDC gene of the present invention exhibits unexpected characteristics and properties. It was found that the gene is expressed in high levels in diversified plant species without disturbing the fertility and morphological development of the plants. Also, substantial homology has been demonstrated between the *C. roseus* tryptophan decarboxylase gene and tyrosine decarboxylase genes from various plant species. This confirms the broad applicability of the present invention which can be extended to tryptophan decarboxylase and tyrosine decarboxylase from a wide variety of plant species.

Also within the scope of the present invention is a transgenic plant having an extrachromosomal gene encoding a plant decarboxylase. This transgenic plant is characterized by having indole glucosinolate levels which are lower than the indole glucosinolate levels of its wild type counterpart. The invention also relates to a transgenic plant seed having an extrachromosomal gene encoding a plant decarboxylase. This transgenic plant seed is also characterized by having indole glucosinolate levels which are lower than the indole glucosinolate levels of its wild type counterpart.

The introduction of a plant gene which encodes tryptophan decarboxylase results in transgenic plants such as canola that redirect tryptophan into tryptamine. Hence, it has been unexpectedly found that the introduction of an extrachromosomal plant TDC gene in host plants can be efficiently used to reduce seed indole glucosinolates in transformed plants by redirection of tryptophan towards an alternative pathway.

Also within the scope of the present invention is a feed composition comprising a rapeseed protein extract from transgenic plants having an extrachromosomal gene encoding a plant decarboxylase. The transgenic plant is characterized by having indole glucosinolate levels which are lower than the indole glucosinolate levels of its wild type counterpart.

IN THE DRAWINGS

FIG. 1 (lane 2) represents the TDC enzymatic activity in extracts of pTDC5-transformed *E. coli*, compared to those in control *E. coli* (lane 1) and that in *C. roseus* itself (lane 3).

FIG. 3 shows the nucleotide sequence of the pTDC5 cDNA clone and its deduced amino acid sequence. The putative polyadenylation signal is underlined.

Figure 7A:
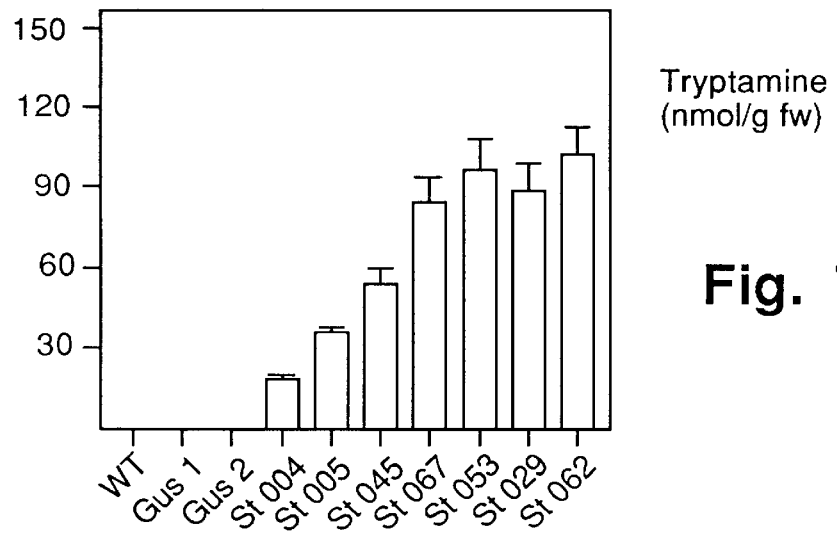
FIG. 7a represents the content of tryptamine in young fully expended leaves of different transgenic canola plants transformed with the *C. roseus* TDC encoding gene of the present invention compared to controls.
Figure 7B:
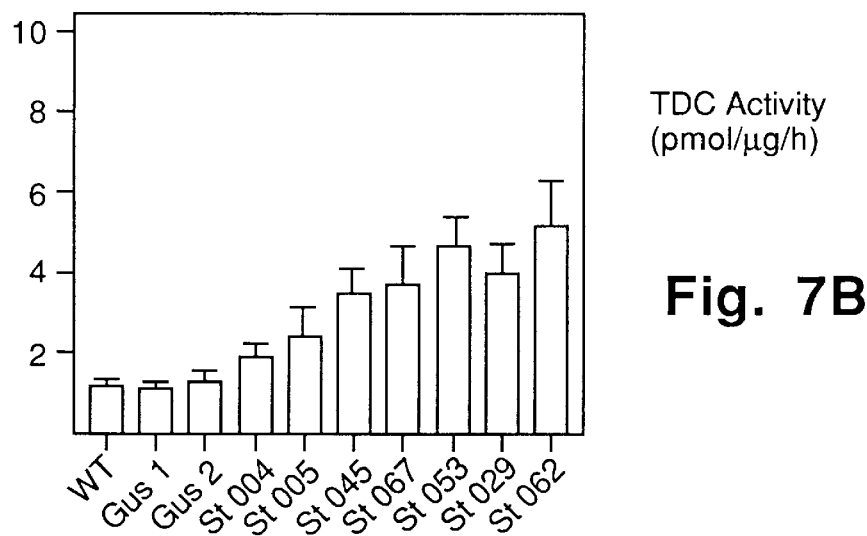

FIG. 7b demonstrates TDC activities in young fully expended leaves of different transgenic canola plants transformed with the *C. roseus* TDC encoding gene of the present invention compared to controls.

Figure 7C:
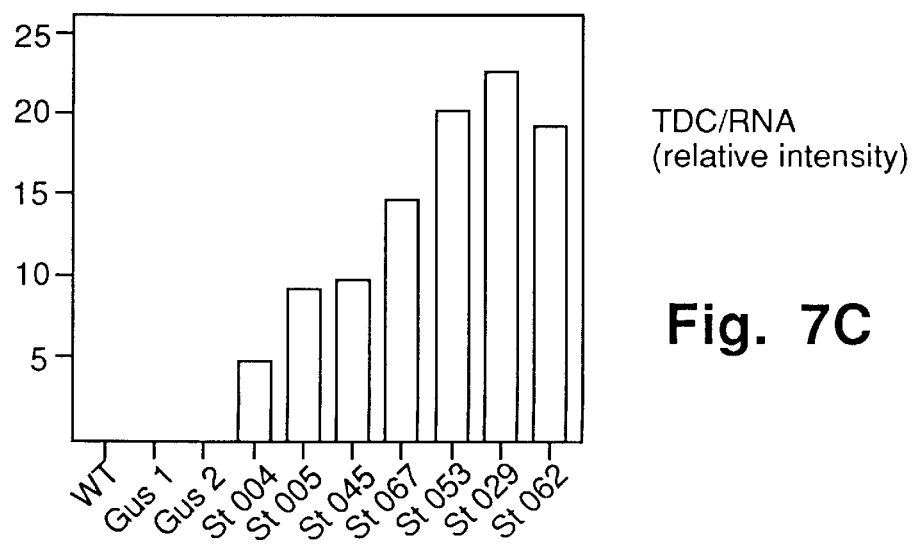

FIG. 7c represents the content of TDC mRNA in young fully expanded leaves of different transgenic canola plants transformed with the *C. roseus* TDC encoding gene of the present invention compared to controls.

Figure 7D:
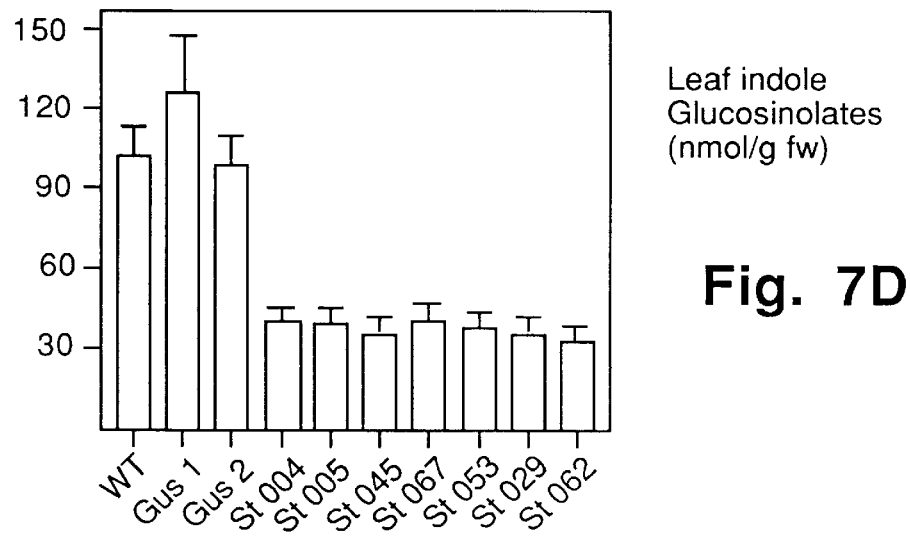

FIG. 7d represents the content of indole glucosinolates in young fully expanded leaves of different transgenic canola plants transformed with the *C. roseus* TDC encoding gene of the present invention compared to controls.

Figure 7E:
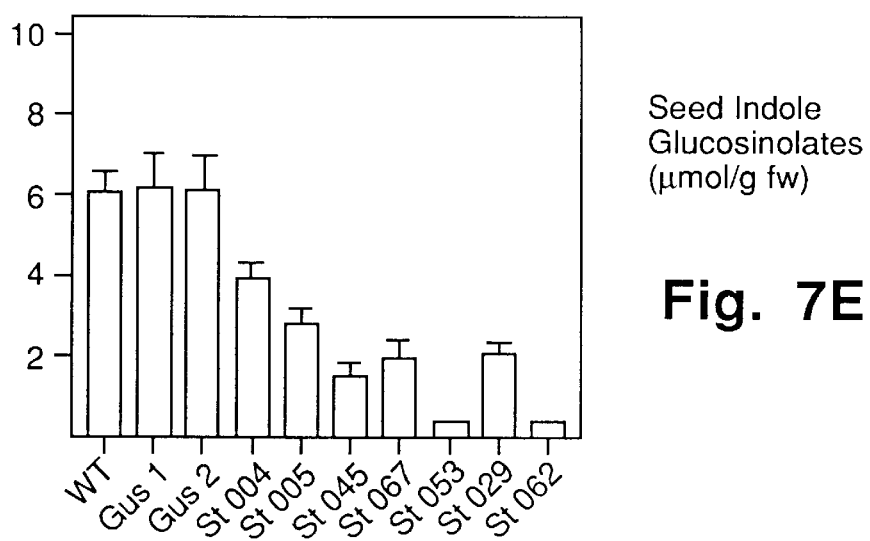

FIG. 7e represents the content of indole glucosinolates in seeds of different transgenic canola plants transformed with the *C. roseus* TDC encoding gene of the present invention compared to controls.

Figure 7F:
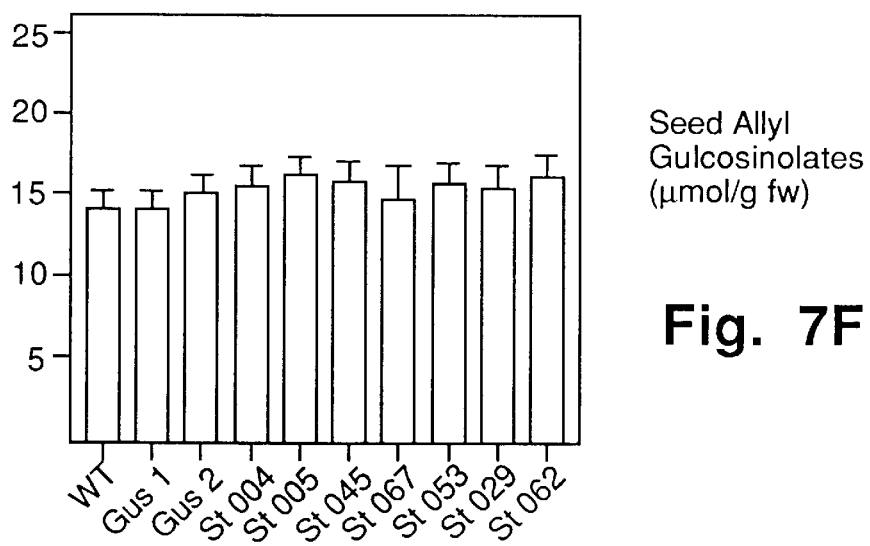

FIG. 7f represents the content of allyl glucosinolates in seeds of different transgenic canola plants transformed with the *C. roseus* TDC encoding gene of the present invention compared to controls.

Figure 8A:
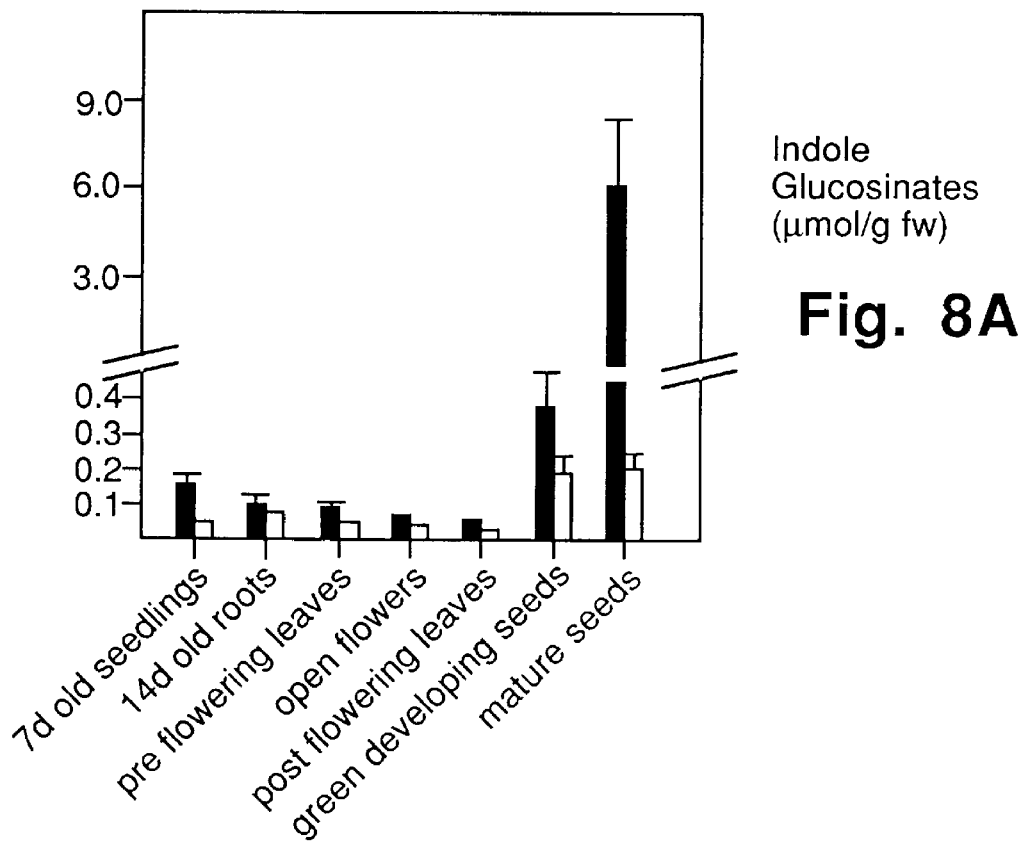

FIG. 8a represents the levels of indole glucosinolates in tryptophan decarboxylase over expressing canola line ST062 compared to non-transformed wild type control plants.

Figure 8B:
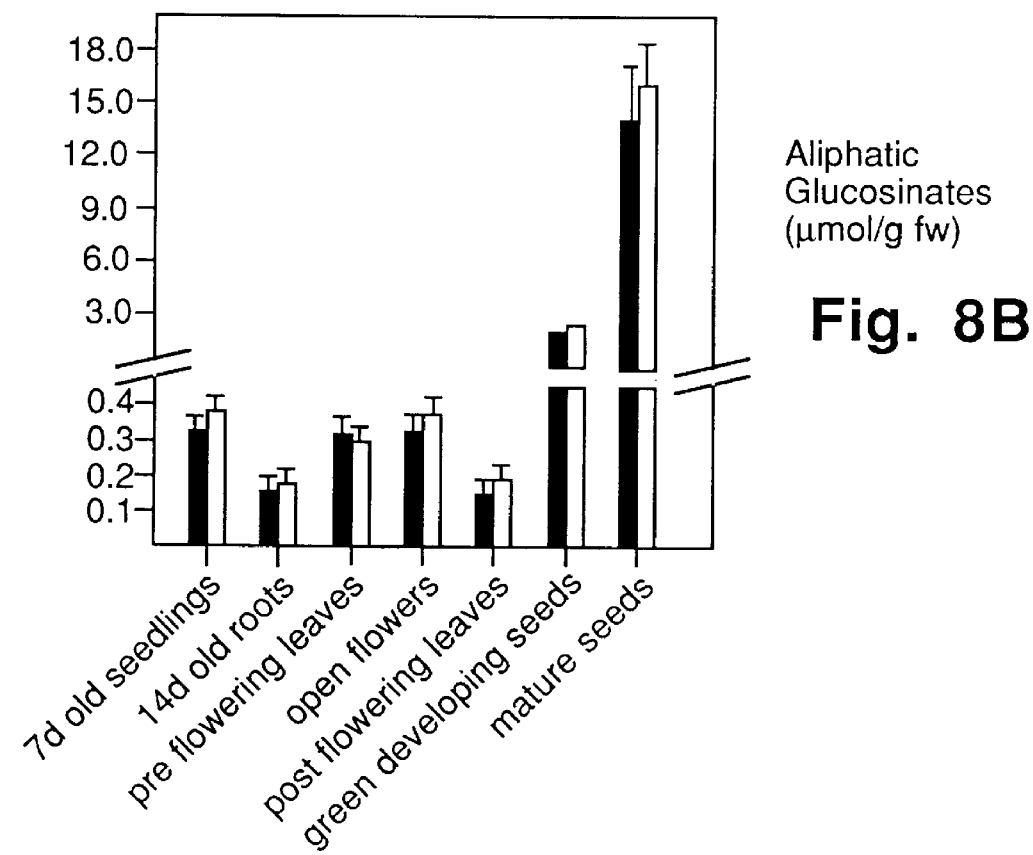

FIG. 8b represents the levels of allyl glucosinolates in tryptophan decarboxylase over expressing canola line ST062 compared to non-transformed wild type control plants.

Figure 8C:
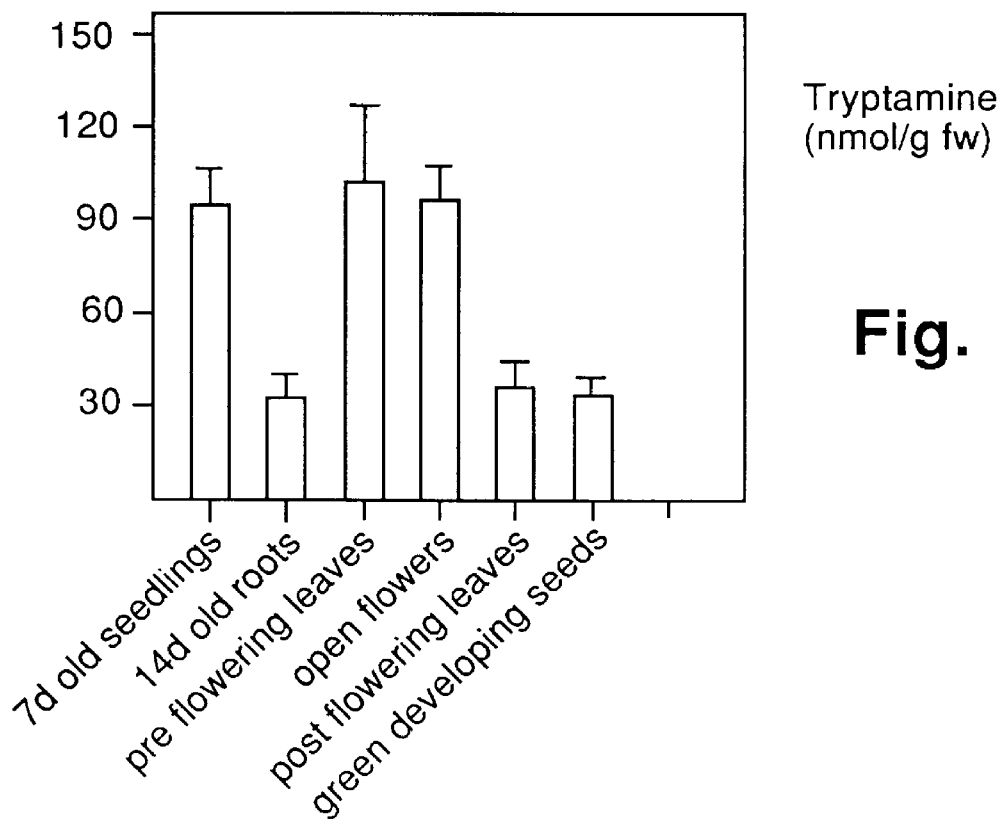

FIG. 8c represents the levels of tryptamine in tryptophan decarboxylase over expressing canola line ST062 compared to non-transformed wild type control plants.

Figure 8D:
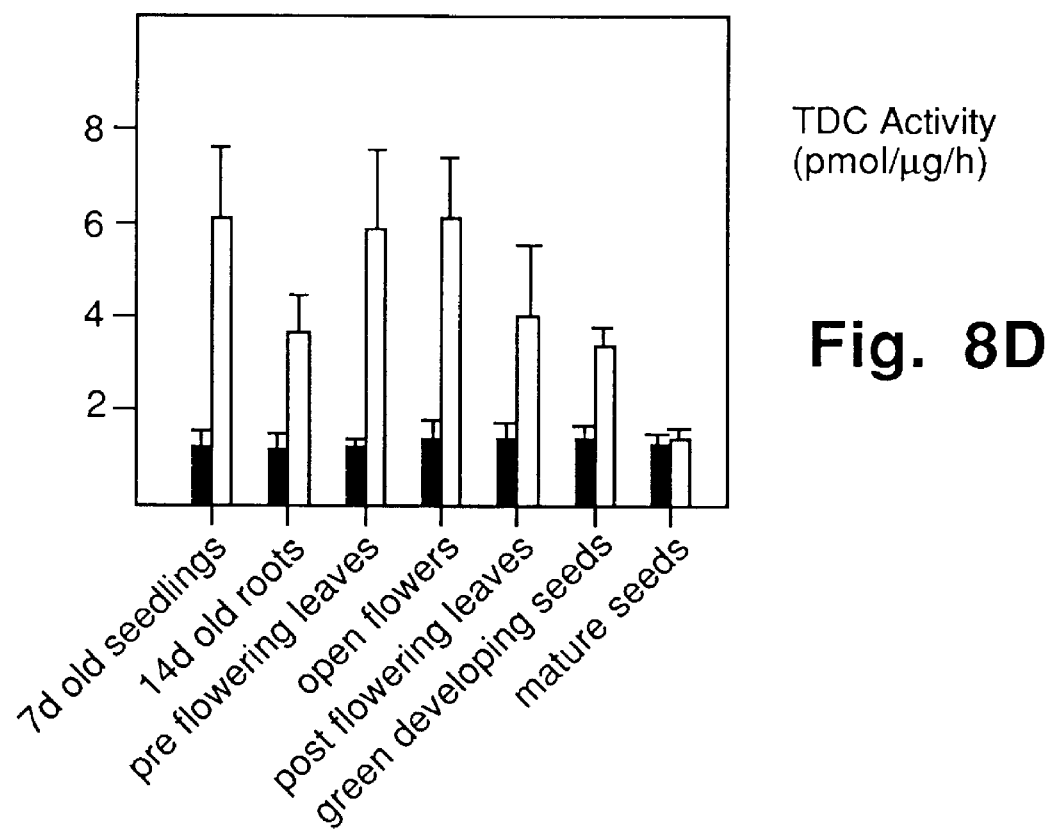

FIG. 8d represents the levels of tryptophan decarboxylase in tryptophan decarboxylase over expressing canola line ST062 compared to non-transformed wild type control plants.

Figure 8E:
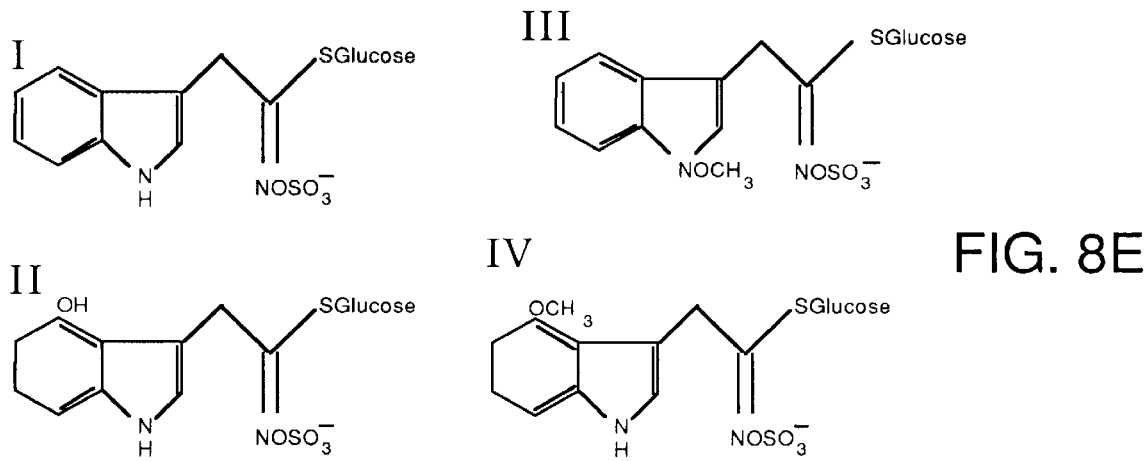

FIG. 8e represents the structures of glucosinolates found in Brassica napus cv. Westar.

Figure 8F:
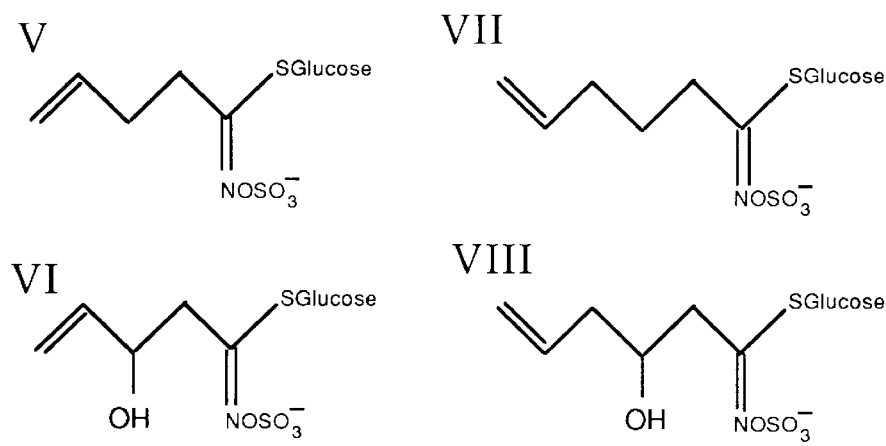

FIG. 8f represents the structures of allyl glucosinolates found in Brassica napus cv. Westar.

Figure 8G:
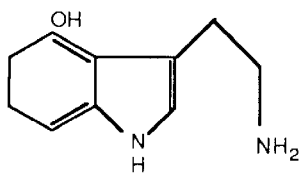

FIG. 8g represents the structures of tryptamine found in Brassica napus cv. Westar.

Figure 8H:
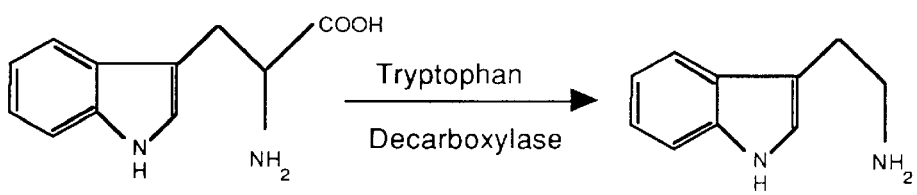

FIG. 8h represents the reaction catalyzed by tryptophan decarboxylase.

DETAILED DESCRIPTION OF THE INVENTION

The present invention relates to a DNA fragment comprising a naturally occurring gene encoding a plant decarboxylase. Preferably, the plant decarboxylase gene is a plant tryptophan decarboxylase gene, more preferably taken from *Catharanthus roseus* and has the nucleotide sequence specified in FIG. 3. The invention also relates to a host microbial or plant cell having an extrachromosomal gene encoding a plant decarboxylase, preferably a tryptophan decarboxylase from *C. roseus*, and to transgenic plants transformed with a plant decarboxylase, preferably a plant tryptophan decarboxylase.

A. Isolation and purification of a plant TDC encoding sequence

The naturally occurring gene comprised in the DNA fragment of the present invention was isolated based on a method which involved purification of the enzyme encoded by the gene in sufficient amounts to allow subsequent manipulations leading to the isolation of the gene. Anti-TDC antibodies were then raised after having purified required amounts of the enzyme to homogeneity. Total RNA was isolated from plant seedlings and double-stranded cDNAs were prepared to produce a recombinant library, which was screened with the polyclonal antiserum raised against TDC to determine the nucleotide sequence of a full-length cDNA clone.

A.1 Purification of the TDC enzyme

Many important factors had to be taken into account when designing an appropriate methodology for isolating and purifying the plant TDC gene. The first step consisted in purifying high levels of a plant TDC protein. The purification of TDC from *C. roseus* cell suspension cultures had been reported previously by Noe and Berlin in (1984) Plant Mol. Biol. 3, 281–288. In this method, several high performance columns were used for protein purification and TDC was isolated from cell cultures which had been transferred to alkaloid production medium. However, the method is very expensive to use and the levels of enzymes purified remained relatively low. Furthermore, even though plant tryptophan decarboxylase had been purified, its actual amino acid sequence was not known. Thus, even though the enzyme had been isolated and its molecular weight determined, the ability to obtain the corresponding gene was far from assured. Indeed, without more information, there was no assurance that the mRNA corresponding to a protein would exist in sufficient quantity or have the required stability to be isolated and characterized.

In the case of the present invention, elicitor-treated cultures, which could be lyophilized without loss of the elicitor-induced TDC enzyme activity, were used. Part of the elicitor-treatment technique used in the context of the present invention is described in Eilert et al. (1987 Archives of Biochemistry and Biophysics 254, No. 2, pages 491–497) which is hereby incorporated by reference. With this technique, fungal elicitors are used to increase the level of TDC protein 10 to 15-fold in cell suspension cultures. Using this method, the purification of TDC could be executed with simple chromatographic steps, and the protocol only required high performance anion-exchange chromatography as a last step to produce TDC in higher yield than reported previously. Indeed, the purification protocol, which is described in detail later on, produced 2 milligrams of pure TDC from 11 g protein per 50 gdw of elicitor-treated cells. This represents a 6-fold improvement in recovery of pure TDC over the previously published methods.

A.2 Production of anti-TDC antibodies

Once sufficient amounts of plant TDC had been purified to homogeneity, plant TDC was mixed with the appropriate adjuvant and injected on several occasions into rabbits in order to raise anti-TDC antibodies for screening the recombinant libraries for TDC production. The production of these polyclonal antibodies, which is described in further detail later on, was not straightforward. Indeed, several rabbits had to be inoculated in order to raise antibodies which can react with different epitopes. Multiple antibodies raised in different animals increase the likelihood that some antibodies will react with the right epitopes on a nitrocellulose-based screening procedure.

A.3 Production of cDNA

After RNA was isolated by chromatography, double-stranded cDNAs were prepared and inserted into the appropriate expression vector. The library of recombinant phages was obtained and, after amplification, plaques were screened with specific polyclonal antiserum raised against TDC. The plasmids containing a TDC cDNA insert were rescued and the nucleotide sequence of a full-length cDNA clone was determined on both strands. It was found that the DNA sequence encoding plant TDC has no introns. Hence, the genomic DNA and cDNA have the same nucleotide sequence.

The immunological screening of bacterially synthesized fusion proteins produced by either plasmid or phage involved two basic technical procedures: the synthesis and immobilization of antigenic material to a solid support, followed by a sensitive detection procedure. The problem that arises in many situations is the fact that the demonstration that a cDNA encodes an antigenic determinant does not necessarily mean that this cDNA encodes the protein of interest. In fact, the sequence of the cDNA clone must be corroborated with the protein sequence of the protein (obtained by protein sequencing) or by homology with another cDNA clone encoding a protein with a similar enzyme activity. In the context of the present invention, as the sequence of the plant TDC protein was not available, the identity of a clone encoding a complete cDNA was demonstrated by showing evidence of TDC activity. In this situation, full-length clones were required in order to produce a full-length protein.

Once the naturally occurring DNA sequence encoding a plant tryptophan decarboxylase has been purified and sequenced, a number of synthetic DNA sequences encoding the same plant tryptophan decarboxylase with a different codon degeneracy can be synthesized based on the naturally occurring DNA sequence. The modifications required to alter codon degeneracy are within the knowledge of the person skilled in the art. These modifications should not substantially alter the resulting amino acid sequence of the enzyme encoded by the DNA sequence to avoid loss of substrate specificity. For example, it is known that most decarboxylases require for their activity a pyridoxal phosphate co-factor linked to the C amino group of a lysine residue. The observed similarities around the pyridoxal binding site of pig kidney decarboxylase, *D. melanogaster*, DOPA-decarboxylase and glutamate decarboxylase with that of *C. roseus* TDC strongly suggests that lysine 319 of TDC binds pyridoxal phosphate. The presence of this site therefore appears to be important to at least maintain an enzymatic activity similar to that specified by the native gene.

B. Confirmation of homology among various plant tyrosine and tryptophan decarboxylase encoding sequences The purpose of this study was to evaluate whether TDC proteins from plant species were substantially homologous from one plant species to another. Substantial homology would allow the use of a TDC encoding sequence from one plant species for obtaining decarboxylase encoding sequences from other plant species. Studies were conducted on protein extracts from opium poppy (*Pappaver somniferum*) to compare decarboxylases from opium poppy to TDC from *C. roseus*.

Similar important regulatory functions have been suggested for tryptophan decarboxylase and tyrosine decarboxylase. For example, in opium poppy, tyrosine decarboxylase participates in morphine alkaloid biosynthesis. As for TDC, it catalyses the synthesis of precursors for protoalkaloids, which have considerable physiological activity in higher animals.

Studies have shown that tyrosine decarboxylase from opium poppy contains epitopes from its protein sequence which are recognized by anti-TDC antibodies. This confirmed similarities between the decarboxylases of *C. roseus* and opium poppy and suggested that there could be sufficient sequence homology between plant decarboxylases to use the TDC cDNA clone isolated from *C. roseus* to clone tryptophan decarboxylases and tyrosine decarboxylases from other species of plants. Subsequent experiments confirmed that there is substantial homology between tyrosine decarboxylase and tryptophan decarboxylases from various plant species. An opium poppy cDNA library was successfully screened with a tryptophan decarboxylase cDNA clone from *C. roseus* to isolate tyrosine decarboxylate from opium poppy. Sequencing of the cDNA from opium poppy encoding tyrosine decarboxylate and comparison with the tryptophan decarboxylase gene from *C. roseus* has shown a homology of at least 55% at the protein level. The substantial homology found both at the cDNA level and at the amino acid level between tyrosine decarboxylate and tryptophan decarboxylates from different species provides convincing evidence of even higher homology among tryptophan decarboxylase from various plant species.

Homology between tryptophan decarboxylase and tyrosine decarboxylase of various plant species was further confirmed in two research publications which subsequently appeared respectively in (1993) Journal of Biological Chemistry, Vol. 268:2189–2194 and in (1993) Plant Molecular Biology, Vol. 21:385–389, hereby incorporated by reference. In the first publication, it was demonstrated that a tyrosine decarboxylase genomic clone which was isolated from parsley plants had significant homology to tryptophan decarboxylase. Indeed, the identity at the protein level between *C. roseus* tryptophan decarboxylase and parsley tyrosine decarboxylase was 275 out of 500 amino acids (55% amino acid sequence identity). In the second paper, it was demonstrated that parsley tyrosine decarboxylase was used to isolate genomic clones of tyrosine decarboxylase from the plant *Arabidopsis thaliana*. This confirmed that the tryptophan decarboxylase clone from *C. roseus* can be used to isolate tryptophan decarboxylase or tyrosine decarboxylase clones from other plant sources.

The DNA sequence encoding a plant TDC was compared with DNA sequences encoding animal decarboxylases and an unexpected 40% amino acid identity was found between the plant and the animal sequences. At the time the research that led to the present invention was completed, a limited amount of plant genes had been cloned and only a few thousand genes from all other sources had been cloned. It was impossible to predict that such a high level of homology would be found between genes encoding similar functions but isolated from highly divergent organisms. In fact, the common wisdom was that encoding TDC sequences from animals and plants would be completely different. Unexpectedly, areas of amino acid similarity extended throughout the protein and were not restricted to a particular portion of either structure. The amino acid sequence similarity could even be extended to the predicted distribution of potential alpha-helix and beta sheets. This indicated that the amino acid differences between the two proteins did not significantly alter their secondary structures and may indicate the importance of such conserved domains to mediate subunits assembly, as well as catalytic function and substrate specificity. This is a further unexpected indication of utility. Indeed, no guidance or motivation was provided to the person skilled in the art to isolate the DNA sequence of the present invention with the expectation that the resulting clone would present such high homology with its animal counterparts. The isolation of the DNA sequence of the present invention was viewed by scientific reviewers as a significant advance in an important area of plant biotechnology that opened up molecular genetic approaches to study the regulation of alkaloid biosynthesis. Another important criteria that led to the acceptance of a manuscript describing the invention for publication in DNAs was the unexpected evolutionary comparison that could be made between plant and animal decarboxylases.

C. Insertion of TDC encoding genes into host plant and bacterial cells

The insertion of TDC genes into plant or bacterial hosts is an important aspect of the present invention. Strategies for practical gene transfer into agriculturally important crops or into important bacteria such as *E. coli* are well-known to those skilled in the art. An example of these strategies for gene transfer into agricultural crops is provided in Horsch et al., in Current Communications in Molecular Biology, Cold Spring Harbour Laboratory 1988, pp. 13–19, hereby incorporated by reference. One of the approaches set forth in this review article was used to introduced a full-length complementary DNA clone encoding tryptophan decarboxylase from *C. roseus* into tobacco, potato and canola. Details on the transformation of tobacco plants with TDC from *C. roseus* are provided in 1990 Plant Physiol. 94:1410–1413, hereby incorporated by reference. In this publication, high levels of tryptamine accumulation in transgenic tobacco expressing tryptophan decarboxylase are demonstrated.

Tryptophan decarboxylase was also produced and tryptamine was accumulated in potato plants (*solanum tuberosum*) and in canola plants (*Brassica napus*) transformed with the TDC encoding gene from *C. roseus*. Table 1 provided below shows TDC activity and tryptamine levels found in potato and canola transformants.

TABLE 1

Expression of tryptophan decarboxylase and accumulation of tryptamine in transgenic potato plants (*Solanum tuberosum*) and in transgenic canola plants (*Brassican napus*)

| Solanum tuberosum | | | Brassica napus | | |
|---|---|---|---|---|---|
| Plant | TDC activity[A] | Tryptamine (g/g fresh wt) | Plant | TDC activity | Tryptamine (μg/g fresh wt) |
| Control | 1.21 | N.D.[B] | Control | 0.89 | N.D. |
| M-9-D-2 | 3.51 | 22.2 | ST-004 | 1.87 | 2 |
| M-9-D-3 | 2.10 | 27.1 | ST-008 | 1.93 | 2.1 |
| M-9-D-5 | 5.23 | 44.2 | ST-015 | 2.15 | 10.4 |
| M-9-D-8 | 15.43 | 42.9 | ST-029 | 4.32 | 15.3 |
| M-9-D-10 | 12.68 | 84.7 | ST-040 | 2.94 | 7.5 |
| M-9-D-11 | 8.46 | 72.5 | ST-042 | 3.55 | 12.5 |
| M-9-D-12 | 9.32 | 47.8 | ST-045 | 3.58 | 14.8 |
| M-9-D-16 | 16.04 | 58.1 | ST-053 | 4.32 | 17.9 |
| M-9-D-21 | 17.23 | 79.8 | ST-062 | 5.41 | 19.0 |
| M-9-D-25 | 16.89 | 94.7 | ST-069 | 4.10 | 14.5 |

[A]Activity in pmole tryptophan converted to tryptamine/μg/hour
[B]N.D. is none detected The DNA fragment encoding a naturally occurring plant TDC gene according to the present invention was found to be expressed at high levels in plant species as diversified as tobacco plants, potato plants, canola plants and even peganum cell cultures (see Berlin et al, 3rd Int. Congress fo Int. Soc. for Plant Molec. Biol. (1991), 1091 for peganum). This demonstrates the possibility of incorporating an extra-chromosomal gene encoding plant TDC in various plant species.

With regard to bacteria, a TDC cDNA clone of *C. roseus* was incorporated in *E. coli* using techniques that are well-known to those skilled in the art. Subsequent assays have shown TDC enzymatic activity in *E. coli*.

D. Characteristics of transformed host plant cells

Despite large amounts of tryptamine accumulated in plants transformed with the DNA isolate of the present invention, the transformed plants were fertile and appeared morphologically normal throughout their development. This is unexpected because tryptophan decarboxylase catalyzes a rate-limiting step in the biosynthesis of indole acetic acid (IAA), one of the 5 major plant hormones (for example, see the review by Reinecke and Bandurski in Plant Hormones and Their Role in Plant Role and Development, 1987, 1988, 1990, Kluwer Academic Publishers, Dordrecht, The Netherlands, pp. 24–42 and the review by Salisbury and Ross in Plant Physiology, 4th Edition, Wadsworth Publishing Company, Belmont, Calif., pp. 357–373, both hereby incorporated by reference). It was impossible to predict whether the level of IAA would be increased as a result of transforming plants with the tryptophan decarboxylase gene. An increase in the levels of this hormone could have proven devastating to plant development and could have interfered with useful utilisation of the TDC gene. Transgenic tobacco plants did not show increased levels of IAA. In fact, the plants show a normal phenotype, except for high levels of tryptamine accumulation. These results are unexpected, given the current level of understanding of plant metabolism.

Tryptophan decarboxylase catalyzes the conversion of tryptophan to tryptamine with the simultaneous release of $CO_2$. The substrate for this reaction, tryptophan, is derived from the central shikimate pathway from which all aromatic amino acids are produced. A majority of plant natural products are derived from aromatic amino acids. Hence, the depletion of tryptophan pools by expression of tryptophan decarboxylase in stable transgenic plants can have important consequences on the levels of available phenylalanine and tyrosine for natural product biosynthesis. The net effect of this may be that the levels of these natural products may actually decrease if sufficient pressure is placed on the tryptophan pools. Creation of plants with an altered chemical spectrum may produce novel phenotypes which have resistance to various pathogenic diseases or to insect pests. This can only be successfully accomplished if a DNA isolate encoding plant TDC can be inserted in various plants and almost systematically provide stable transformants. This is what has been achieved for the first time with the present invention.

One of the unexpected achievements of the insertion of extrachromosomal plant decarboxylase genes into plants was the production of transgenic plants having substantially reduced levels of indole glucosinolate while maintaining unaltered levels of allyl glucosinolate. Analysis have demonstrated a clear relationship between the activity of the extrachromosomal TDC gene and the lower indole glucosinolate levels accumulating in different plant parts. Even more unexpected is the fact that the decreased availability of tryptophan for indole glucosinolate biosynthesis has no significant effects on the production and accumulation of the methionine-derived allyl glucosinolates. The similarity in allyl glucosinolate contents of transgenic and control roots, leaves, open flowers and developing seedlings also support the hypothesis that different biosynthetic mechanisms may be involved for the production of indole and allyl-glucosinolates.

The use of genetic engineering to redirect tryptophan away from indole glucosinolates in plants demonstrates how the biosynthetic pathway leading to an undesirable product can be intercepted. The results suggest that multiple sinks are simultaneously available for carbon, nitrogen and other resources in plants, and their relative levels can be manipulated by redirecting metabolite flow at key branch points.

Except for the altered chemistry reported previously, all of the transgenic plants developed in the context of the present invention grew and developed at the same rate and appeared identical to the non-transformed control plants under greenhouse conditions. The time to flower, the number of flowers produced, and the time to produce seed was identical and seeds appeared normal with respect to size and appearance.

The ability of transgenic lines of plants to grow normally suggests that only tryptophan destined to accumulate as indole glucosinolates is redirected. If this is the case, then the redirection of branch point substrates might also be useful in decreasing levels of other undesirable secondary metabolites, such as the allyl glucosinolates of canola and the toxic cyanogenic glucosides in major crops like sorghum and cassava. The potential applications of this strategy are numerous and offer alternative solutions to problems often treated by antisense approaches.

The availability of canola or other Brassica crops with reduced indole glucosinolates is also useful to study the effectiveness of altered chemistry on insect deterrence. Several studies have indicated that insect behavior can be affected by Brassica leaf chemistry and these precisely altered transgenic plants can also provide promising new tools to obtain a better understanding of plant-insect interactions.

DESCRIPTION OF PREFERRED EMBODIMENTS a) Isolation of tryptophan decarboxylase from *C. roseus*

1° Growth of cell suspension cultures

Cell line No. 615 was initiated in 1979 from anther explants of greenhouse-grown *Catharanthus roseus* (L.) G. Don vc Little Delicata plants, and this cell line produced indole alkaloids when transferred to alkaloid production medium (Kurz et al. (1980), Alkaloid production in *Catharanthus roseus* cell cultures; initial studies on cell lines and their alkaloid content, Phytochemistry 19:2583–2587). Cells were grown in the medium of Gamborg et al. (1968, Nutrient requirements of suspension cultures of soybean root cells, Exp. Cell Res. 50:151–158) with 1 mg/L 2,4-D (1B5) in 10 L fermentors. After 8 d of growth, cells were treated with *Pythium aphanidermatum* fungal elicitor (5 mL/100 mL of cells) as described in Eilert et al., 1987, Elicitor-mediated induction of tryptophan decarboxylase and strictosidine synthase activities in cell suspension cultures of *Catharanthus roseus*, Arch. Biochem. Biophys. 254:491–497. Elicitor treatment resulted in a rapid induction of tryptophan decarboxylase activity. Cells were harvested and the medium was removed by filtration on Büchner funnels under suction (Whatman No. 1 filter paper). The wet cell mass was lyophilized and was used as an enzyme source.

2° Purification to homogeneity of TDC isolated from *C. roseus* cell suspension cultures Lyophilized elicitor-treated *C. roseus* cells (line 615) (about 50 gdw/500 gfw) were homogenized with a Polytron probe in 500 mL of 0.1M Tris-HCl (pH 7.5) containing 20 mg/L PMSF, 1.9 g/L sodium metabisulfite, 2 g/L EDTA, 300 mg/L DTT, 3.33 g/L PVPP, 10 g/L Dowex 1×2 resin (pre-equilibrated in 0.1M Tris-HCl, pH 7.5), 0.02% $NaN_3$, and 50 mg/L pyridoxal phosphate. An additional 40 to 50% of TDC enzyme activity was recovered by reextracting the pellet after centrifugation. All purification steps were carried out at 4° C. The crude extract was centrifuged at 10,000 rpm for 10 min, and the resulting supernatant was fractionated with ammonium sulfate between 40 and 60% saturation at 4° C. The 60% pellet was back extracted with 40% saturated $NH_4SO_4$ in 50 mM Tris-HCl (pH 8), 0.1% β-mercaptoethanol, and 0.02% $NaN_3$ (buffer A), and the extract was centrifuged at 10,000 rpm for 10 min. The supernatant was treated with ammonium sulfate to 60% saturation and the extract was centrifuged at 10,000 rpm for 10 min. The pellet was dissolved in 5 mL buffer A and was desalted on a Sephadex-G25 column (2.5×22 cm) in buffer A. Active fractions were pooled and 40% polyethylene glycol-7000 was added to a final concentration of 12%. After centrifugation at 10,000 rpm for 10 min, the pellet was discarded, and the supernatant was loaded onto DEAE-Sephacel (2.5×7 cm) in buffer A. Protein was eluted using a 600 mL gradient (0–0.3M NaCl) and TDC enzyme activity was recovered between 0.1 to 0.15M NaCl. Active fractions were pooled and TDC was precipitated by adding ammonium sulfate to 65% saturation followed by centrifugation at 10,000 rpm for 10 min. The pellet was dissolved in 3 mL of 20 mM bis-Tris (pH 6.9) containing 0.1% β-mercaptoethanol (buffer B), and the solution was loaded onto Sephacryl S-300 (2.5×9.3 cm) in buffer B. Active fractions were pooled (15 mL) and were loaded directly onto Mono Q HR 5/5 high performance anion exchanger equilibrated with buffer B. TDC enzyme activity was eluted with a linear gradient 0 to 0.25M KCl in 50 mL buffer B. Approximately 2 mg of pure TDC was recovered by this purification protocol.

3° Production of antibodies against TDC, enzyme-linked immunoassay (ELISA)

Rabbits were immunized with 200 μg of purified TDC using Freund's adjuvant, and after three booster injections at biweekly intervals, antibodies of higher titer against TDC were obtained.

Figure 1:
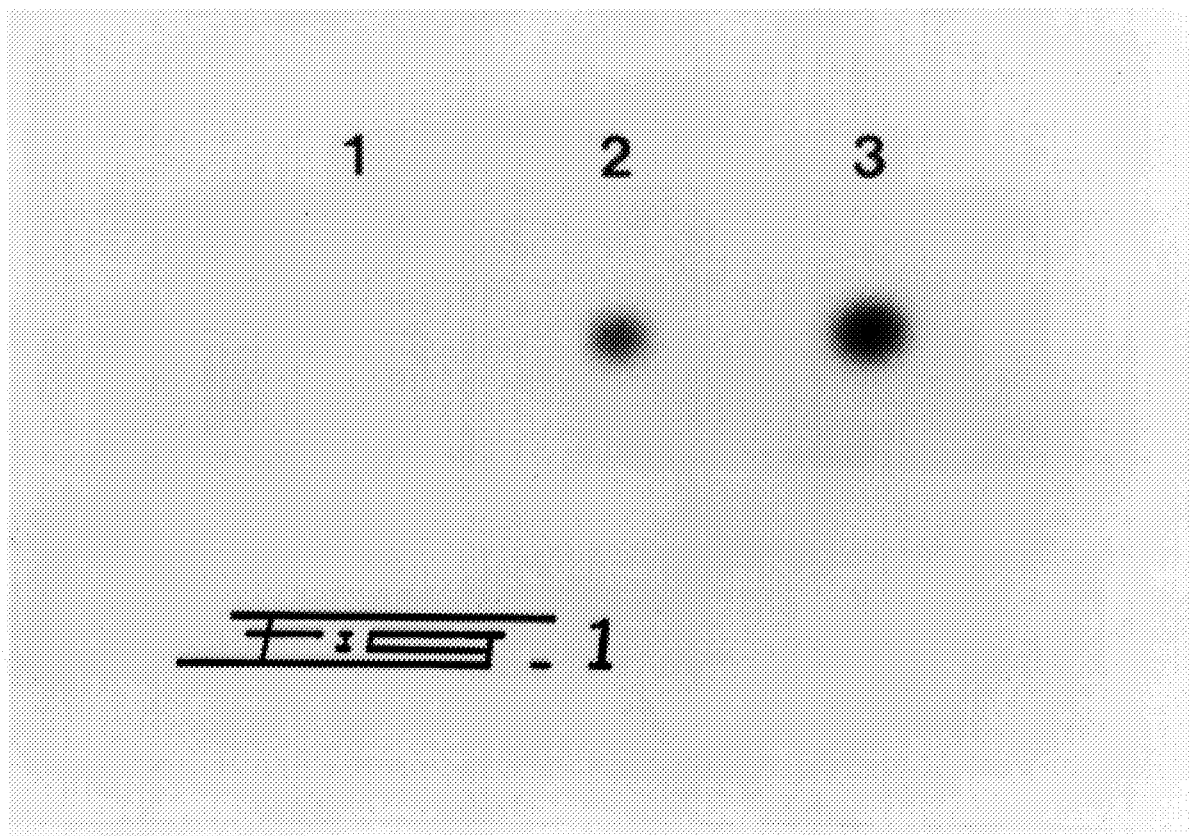

Quantitation of TDC antigen was performed by direct ELISA (Engvall E., 1980, Enzyme immunoassay ELISA and EMIT, Methods Enzymol. 70:419–439) which could detect TDC antigen below levels of 20 ng/microtiter well (FIG. 1). Microtiter plates (Dynatech instruments) were routinely coated overnight at 4° C. with known quantities of pure TDC next to the unknown samples which were to be determined (final volume 200 μL of 0.1M $NaHCO_3$, 0.05M $NaN_3$ [pH 9.6] per well). After inactivation of remaining binding sites with 2% BSA in buffer C (0.25M NaCl, 10 mM Tris, 0.05M $NaN_3$, 0.08% Tween 20 [pH 8]) and washing three times with buffer C, the samples were reacted with anti-TDC antibody diluted 10,000-fold in buffer C containing 0.1% BSA (200 μL per well). After incubation at 37° C. for 2 h and washing the plates three times in buffer C, the samples were reacted with second antibody (goat anti-rabbit antibodies conjugated to alkaline phosphatase) (200 μL per well) diluted 3,000-fold in buffer C. Plates were washed three times in buffer C after a 1 h incubation at 37° C. in second antibody. Substrate solution (P-nitro-phenyl phosphate at 1 mg/mL in 1M diethanolamine, 1 mM $MgCl_2$, 0.05% $NaN_3$ [pH10], 200 μL/well) was added and reactions were allowed to proceed for up to 1 h, after which reactions were stopped with 20 μL of 1M NaOH. Color production was read in an automatic ELISA reader at 410 nanometers.

4° Electrophoresis and immunoblotting

Native or SDS-PAGE (10%) was performed (Chrambach et al., 1976, Analytical and preparative polyacrylamide gel electrophoresis. An objectively defined fractionation route, apparatus, and procedures. In N Castsimpoolas, ed. Methods of Protein Separation, Vol. 2, Plenum, New York, pp. 27–144), and proteins were transferred onto nitrocellulose membranes (Shcleicher & Schull) (Towbin et al., 1979, Electrophoretic transfer of proteins from polyacrylamide gels to nitrocellulose sheets: procedure and some applications, Proc. Natl. Acad. Sci. USA 76:4350–4354). The protein blot was rinsed with distilled water and incubated 3 h at 37° C. in buffer E containing 5% w/v skim milk powder (Johnson et al., 1984, Improved technique utilizing nonfat dry milk for analysis of proteins and nucleic acids transferred to nitrocellulose, Gene Anal. Techn. 1:3–8), 1% v/v Tween-20 in PBS at pH 7.5. Anti-TDC antibody was diluted 1:2000 in buffer E and was added to the nitrocellulose sheets for overnight incubation at 4° C. After extensive washing with buffer E, the nitrocellulose sheets were incubated for 2 h with goat anti-rabbit IgG-conjugated alkaline phosphatase diluted 1:1000 in buffer E. The sheets were extensively washed with buffer E and were finally washed one time in buffer G (150 mM $Na_3CO_3$ [pH 9.6]. TDC antigen could be detected when assaying for bound alkaline phosphatase after incubation with nitro blue tetrazolium (0.1% w/v) and chloroindonyl phosphate (dissolved in dimethyl formamide)(0.005% w/v) in buffer G.

5° Purification and properties of TDC

The purification of TDC was performed successively using elicitor-treated cell suspension cultures. These treated cultures were used as a source for TDC since they contained 15- to 20-fold higher levels of this enzyme than untreated cells (as described in Eilert et al. mentioned above). The purification protocol described previously produced 2 mg of pure TDC from 11 g protein per 50 gdw of elicitor-treated cells. This represents a 6-fold improvement in recovery of pure TDC over a previously published method (Noe et al., 1984, Tryptophan decarboxylase from *Catharanthus roseus* cell suspension cultures: purification, molecular and kinetic data of the homogeneous protein, Plant Mol. biol. 3:281–288).

The purified TDC migrated as a dimer on Superose 12 high performance chromatography and had a mol wt of 110,000. TDC subunit mol wt of the protein, as estimated by SDA-PAGE, was 55,000. Electrophoresis of the protein on 7.5% native gels at 4° C. and enzyme assay for TDC activity accounted for by the gel slice corresponding to the pure TDC band. Other properties of the purified TDC were the same as those reported previously, as described in Noe et al. as mentioned above.

b) cDNA synthesis and DNA sequencing

Seedlings of *C. roseus* (L.) G. Don cv "Little Delicata" were germinated and grown for 5 days in the dark as described previously (De Luca, V., Alvarez-Fernandez, F., Campbell, D., & Kurz, W. G. W. (1988) Plant Physiol. 86, 447–450). Seedlings were harvested after 18 hours of light treatment and total RNA was isolated as described by Jones, J. D. G., Dunsmuir, P. & Bedrook, J. (1985) EMBO J. 4, 2411–2418.

Poly(A)$^+$ RNA was isolated by chromatography on oligo (dT)$^-$ cellulose (Aviv, H. & Leder, P. (1972) Proc. Natl. Acad. Sci. USA 69, 1408–1412) and double-stranded cDNAs were prepared according to the procedure of Gubler and Hoffman (1983, Gene 25, 263–269). Following ligation with Eco RI linker, the cDNA was inserted into the Eco RI site of the expression vector ZAP (Stratagene, San Diego, Short, J. M., Fernandez, J. M., Sorge, J. A. & Huse, W. D. (1988) Nucl. Acids Res. 16, 7583–7600). A library containing $3.1 \times 10^5$ recombinant phages was obtained and after amplification, $2 \times 10^5$ plaques were screened with specific polyclonal antiserum raised against-TDC. Plasmids (pBluescript) containing a TDC cDNA insert were rescued using the R408 fl helper phage (Short, J. M., Fernandez, J. M., Sorge, J. A. & Huse, W. D. (1988) Nucl. Acids Res. 16, 7583–7600) and the nucleotide sequence of a full-length cDNA clone (pTDC5) was determined on both strands by the dideoxy-chain-termination method (Sanger, F., Nicklen, S. & Coulson, A. R. (1977) Proc. Natl. Acad. Sci. USA 74, 5463–5467). The sequencing strategy included subcloning of restriction fragments and the use of oligonucleotide primers. The sequence for all restriction sites used for the subcloning was determined on at least one strand. Comparisons of the pTDC5 cDNA nucleotide sequence and of the deduced amino acid sequence with Genbank and NBRF sequence libraries were performed using the FASTA program package (Pearson, W. R. & Lipman, D. J. (1988) Proc. Natl. Acad. Sci. USA 85, 2444–2448).

c) RNA blot hybridization

Poly(A)$^+$ RNA was isolated from 6 day old developing seedlings (see (1992) Plant Cell Reports 11:86–89) and from young leaves of mature plants as described above. These tissues were chosen as a likely source of TDC poly(A)$^+$ RNA based on the presence of high levels of TDC enzyme activity (De Luca, V., Alvarez-Fernandez, F., Campbell, D., & Kurz, W. G. W. (1988) Plant Physiol. 86, 447–450). RNA was denatured, fractioned by electrophoresis on formaldehyde/agarose gels, and then transferred to nitrocellulose filters (Maniatis, T., Fritsch, E. F. & Sambrook, J. (1982) In: Molecular Cloning, A Laboratory Manual. Cold Spring Harbor, N.Y.). Blotted RNA was hybridized to [$^{32}$P]-labelled pTDC5 DNA and autoradiography was performed using Kodak XAR-5 films.

d) TDC activity in extracts of E. coli

A culture (100 ml) of the E. coli strain XL1-blue containing pTDC5 or pBluescript was incubated at 37° C. for 2 hours before adding the IPTG inducer at a final concentration of 1 mM. Incubation was continued for an additional 2 hours. Cells were harvested, washed in TE buffer, resuspended and lysed in 3 ml of a buffer containing 0.1M Hepes, pH 7.5, 1 mM DTT. Debris was removed by centrifugation and the supernatant was desalted by passage over a Sephadex G-25™ column. TDC enzymatic activity in bacterial supernatants was determined by monitoring the conversion of L-[methylene-$^{14}$C]-tryptophan to [$^{14}$C]-tryptamine (De Luca, V., Alvarez-Fernandez, F., Campbell, D., & Kurz, W. G. W. (1988) Plant Physiol. 86, 447–450). Supernatants (30 µl) were incubated in the presence of 0.1 µCi of [$^{14}$C]-tryptophan (sp. act. 59 mCi/mmol.) for 30 minutes and reactions were stopped with 100 µl NaOH. Radioactive tryptamine was extracted from the reaction mixture with ethyl acetate and was analyzed by silica gel thin layer chromatography and autoradiography. Determination of TDC enzyme activity in leaves was performed as described previously (De Luca, V., Alvarez-Fernandez, F., Campbell, D., & Kurz, W. G. W. (1988) Plant Physiol. 86, 447–450).

e) TDC enzymatic activity in E. coli

A tryptophan decarboxylase cDNA clone of C. roseus was isolated by the use of antibody screening of an expression library. The antigenicity and enzymatic activity (FIG. 1) of the encoded protein established the identity of the TDC cDNA.

When the original cDNA library was screened with the anti-TDC antibody, 27 clones were identified. Six clones were selected and submitted to further analysis. Partial sequence analysis revealed no difference among these clones, except for their length. Therefore, the clone having the longest cDNA insert (pTDC5) was selected for further characterization. To confirm that this cDNA clone corresponded to TDC, enzymatic activity was measured in cell extracts from E. coli. FIG. 1 shows that [$^{14}$C]-tryptamine was produced with extracts from cells transformed with pTDC5, and with extracts from C. roseus leaves (lane 3), but not with extracts from cells containing only the vector (lane 1).

The conversion of [$^{14}$C]-tryptophan to [$^{14}$C]-tryptamine was monitored in extracts of E. coli and C. roseus leaves. [$^{14}$C]-tryptophan (sp. act. 50 mCi/mmol) for 30 minutes. After addition of base, [$^{14}$C]-tryptamine was extracted from the reaction mixture with ethyl acetate and reaction products were analyzed by thin layer chromatography on silica gel (solvent CHCl$_3$ MeOH: 25% NH$_3$ (5:4:1) and autoradiography. In FIG. 1, TDC enzymatic activity is shown; lane 1, E. coli is transformed by the pBluescript vector, lane 2, E. coli is transformed by pTDC5 and lane 3, C. roseus extract is shown.

This result indicated that TDC enzymatic activity was retained by the protein produced using a TDC cDNA clone under the control of the Lac promoter of the pBluescript vector. No attempts were made to quantify the level of activity of TDC in E. coli.

f) Sequence analysis of a TDC cDNA clone

Figure 2:
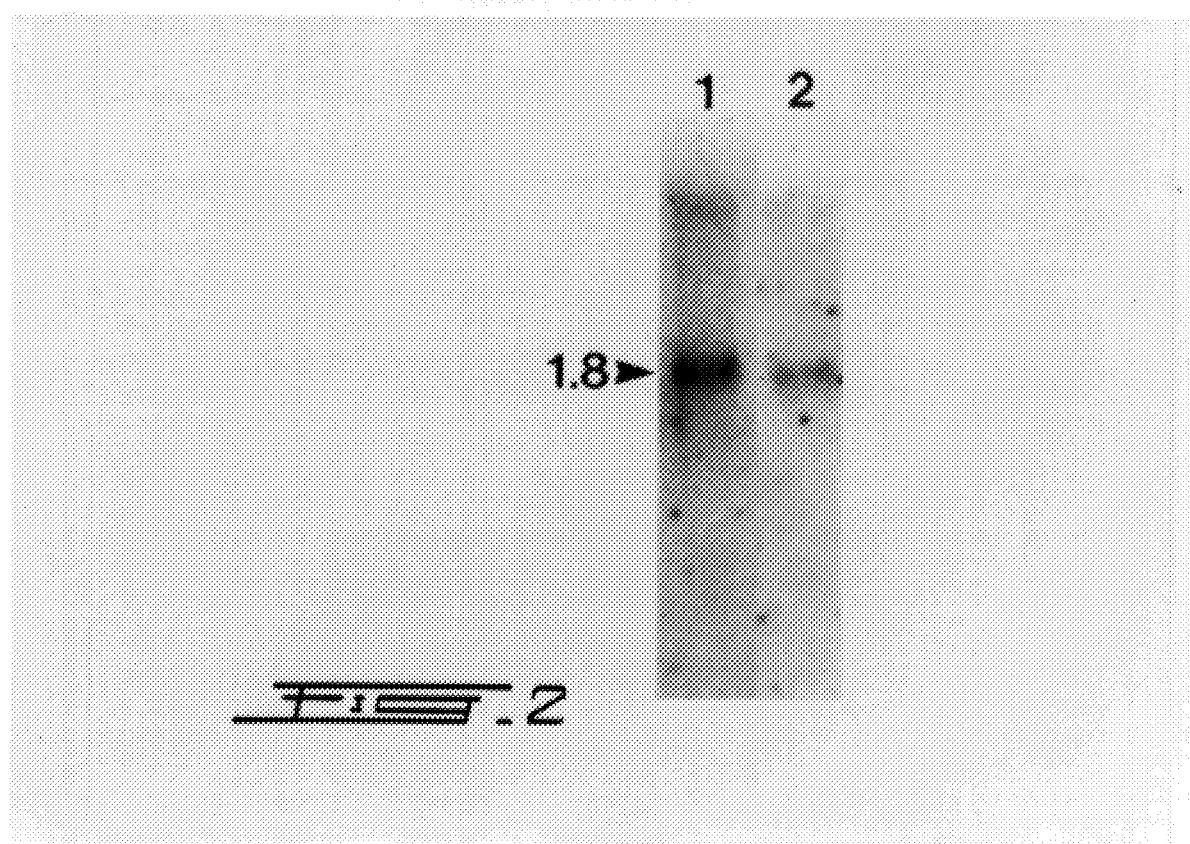
FIG. 2 represents the hybridization of the pTDC-5 clone to a 1.8 kb mRNA species isolated from periwinkle.

DNA sequence analysis of pTDC5 revealed the presence of an open reading frame coding for a protein of 500 amino acids, which corresponded to a molecular mass of 56,142 Da (FIG. 2). The 5'-nontranslated region of pTDC5 contained 69 nucleotides and included, near its beginning, a long stretch of alternating pyrimidines. Sequence around the methionine initiation codon (AAUAAUGGG) matched closely the consensus sequence for plant gene initiation codons (AACAAUGGC) (Lütcke, H. A., Chow, K. C., Mickel, F. S., Moss, K. A., Kerm, H. F. and Scheele, G. A. (1987) EMBO J. 6, 43–48). The 3'nontranslated region consisted of 168 nucleotides up to the poly(A) tail and contained an AAUAAA putative poly(A)$^+$ addition signal 17 nucleotides upstream from the start of the poly(A)$^+$ tail. Examination of the predicted amino acid sequence did not reveal the presence of a signal sequence (Watson, M. E. E. (1984) Nucl. Acids Res. 12, 5145–5164), which is consistent with the proposed cytoplasmic location of TDC within the cell (De Luca, V., Alvarez-Fernandez, F., Campbell, D., & Kurz, W. G. W. (1988) Plant Physiol. 86, 4474–50).

Comparison of TDC-cDNA nucleotide and deduced amino acid sequences with nucleotide sequences in the Genbank DNA sequence database and with amino acid sequences in the NBRF protein sequence database revealed surprising similarity (40% amino acid identity) with the dopa-decarboxylase isoenzyme 1(DDC1) from D. melanogaster (Eveleth, D. D., Gietz, R. D., Spencer, C. A., Nargang, F. E., Hodgetts, R. B. & Marsh, J. L. (1986) EMBO J. 5, 2663–2672; Morgan, B. A., Johnson, W. A. & Hirsh, J. (1986) EMBO J. 5, 3335–3342), and with the protein corresponding to the D. melanogaster alpha-methyldopa hypersensitive gene (AMD, 35% amino acid identity) (Eveleth, D. D. & Marsh, J. L. (1986) Genetics 114, 469–483) (FIG. 3). In FIG. 3, the boxes show TDC residues present in AMD and/or DDC1 sequences. Amino acids are numbered for TDC (top) and DDC1 (bottom). The areas of amino acid similarity extended throughout the protein and were not restricted to a particular portion of either structure.

Furthermore, the 39% amino acid sequence similarity could be extended to the predicted distribution of potential alpha helices and beta sheets. This indicated that the amino acid differences between the two proteins did not significantly alter their secondary structures, and may indicate the importance of such conserved domains to mediate subunit assembly, as well as catalytic function and substrate specificity. This unexpected 40% amino acid identity between the plant and animal TDC sequence suggests a possible evolutionary link between these decarboxylases.

Limited proteolysis of pig kidney dopa decarboxylase and amino acid sequencing of a tryptic fragment produced a sequence for 50 amino acid residues one third of the distance from the COOH terminus of this protein (Tancini, B., Dominici, P., Simmaco, M., Schinina, M. E., Barra, D., & Voltatormi, C. D. (1988) Arch. Biochem. Biophys. 260, 569–576). Comparison of this 50 amino acid sequence with periwinkle TDC and *D. melanogaster* DDCI gave 20 and 32 identical amino acids, respectively. Furthermore, comparison of *C. roseus* TDC to feline glutamic acid decarboxylase (Kobayashi, Y., Kaufman, D. L. & Tobin, A. J. (1987) J. Neurosci. 7, 2768–2772) showed that 10% of the amino acid residues were identical between these two proteins. This similarity could be extended to 25% on a 396 aa stretch. Mouse ornithine decarboxylase (Kahana, C. & Nathans, D. (1985) Proc. Natl. Acad. Sci. USA 82, 1673–1677) showed a statistically significant (Pearson, W. R. & Lipman, D. J. (1988) Proc. Natl. Acad. Sci. USA 85, 2444–2448) 12% amino acid sequence similarity to the plant TDC which also extended throughout the protein sequence. We also found that the sequence Pro-His-Lys, beginning at position 317 in TDC, was identical to the sequence at the pyridoxal phosphate binding sites of *D. melanogaster* DDC (Marques, I. A., & Brodelius, P. (1988) Plant Physiol. 88, 52–55; Clark, W. C., Pass, P. S., Venkataraman, B., & Hodgetts, R. B. (1978) Mol. Gen. Genet. 162, 287–297), feline glutamic acid decarboxylase (Kobayashi, Y., Kaufman, D. L. & Tobin, A. J. (1987) J. Neurosci. 7, 2768–2772) and pig dopa-decarboxylase (Bossa, F., Martini, F., Barra, D., Borri Voltatorni, C., Minelli, A. & Turano, C., (1977) Biochem. Biophys. Res. Commun. 78, 177–183). In contrast, the AMD protein, whose enzymatic function is unknown, contained the sequence Leu-His-Lys at the pyridoxal phosphate binding domain. The sequence similarity observed between TDC, feline glutamic acid decarboxylase and mouse ornithine decarboxylase also suggests an evolutionary link between these three amino acid decarboxylases.

Figure 4A:
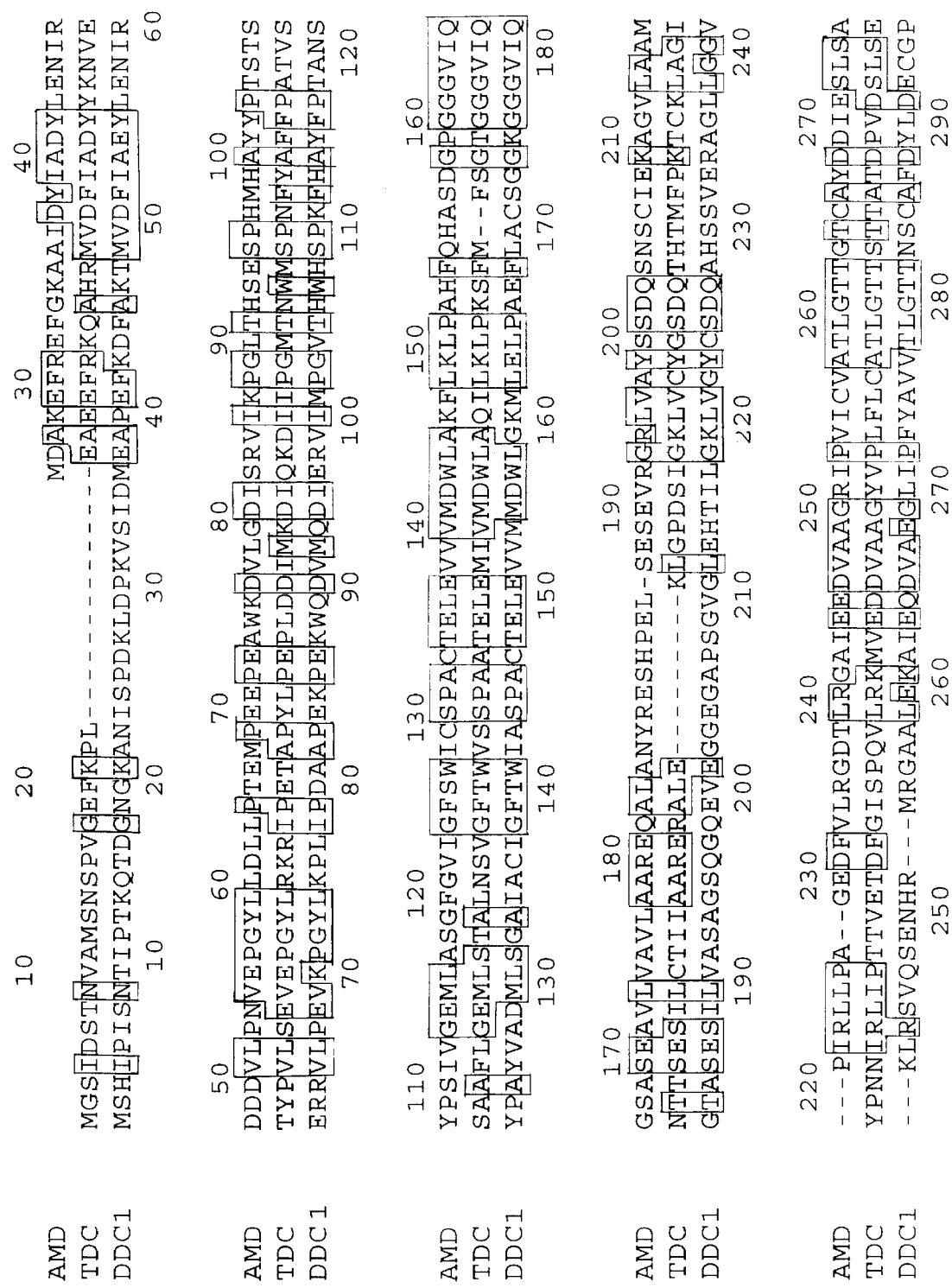
FIG. 4 shows the amino acid sequence alignments of the protein for the *D. melanogaster* alpha methyldopa hypersensitive gene (AMD), *C. roseus* tryptophan decarboxylase (TDC), and Drosphila DOPA decarboxylase isoenzyme 1 (DDC1).

Structural similarities between TDC and *D. melanogaster* DDC1 proteins were further revealed by comparing their hydropathy profiles (FIG. 4). Each value was calculated as the average hydropathic index of a sequence of 9 amino acids and plotted to the middle residue of each sequence. Positive and negative values indicate hydrophobic and hydrophillic regions of the proteins, respectively. Close examination of the alignment of hydrophobic and hydrophillic regions for the two proteins showed a striking match between them, except for the area near the N terminus and the region around TDC residue 225.

Most decarboxylases require for their activity a pyridoxal phosphate co-factor linked to the C amino group of a lysine residue. The observed similarities around the pyridoxal binding site of pig kidney dopa-decarboxylase, *D. melanogaster* dopa-decarboxylase and feline glutamate decarboxylase with that of periwinkle TDC strongly suggests that lysine 319 of TDC binds pyridoxal phosphate.

The aromatic amino acid decarboxylases of plants, insects and mammals are remarkably similar in subunit structure, molecular mass and kinetic properties (Maneckjee, R., & Baylin, S. B. (1983) Biochemistry 22, 6058–6063). Plant aromatic amino acid decarboxylases (Noe, W., Mollenschott, C. & Berline J. (1984) Plant Mol. Biol. 3, pages 281–288; Chapple, C. C. S., (1984) Ph.D. Thesis, University of Guelph, Guelph, Ontario, Canada; Marques, I. A., & Brodelius, P. (1988) Plant Physiol. 88, pages 52–55), in contrast to those from animals, display high substrate specificity for indole or aromatic substrates but not to both. The strong similarity observed between periwinkle TDC and DDC1 of *D. melanogaster* suggests that plant aromatic amino acid decarboxylase specific for tyrosine, phenylalanine or dihydroxyphenylalanine may be structurally similar to TDC and may, therefore, also be evolutionarily related.

g) TDC mRNA accumulation

Figure 5A:
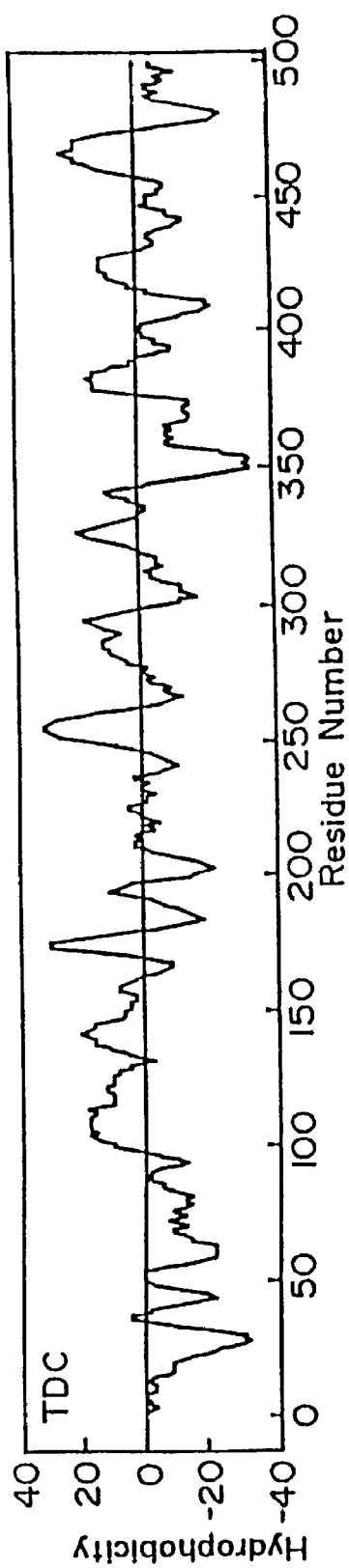
FIG. 5 shows hydropathy profile of TDC and DDC1.
Figure 5B:
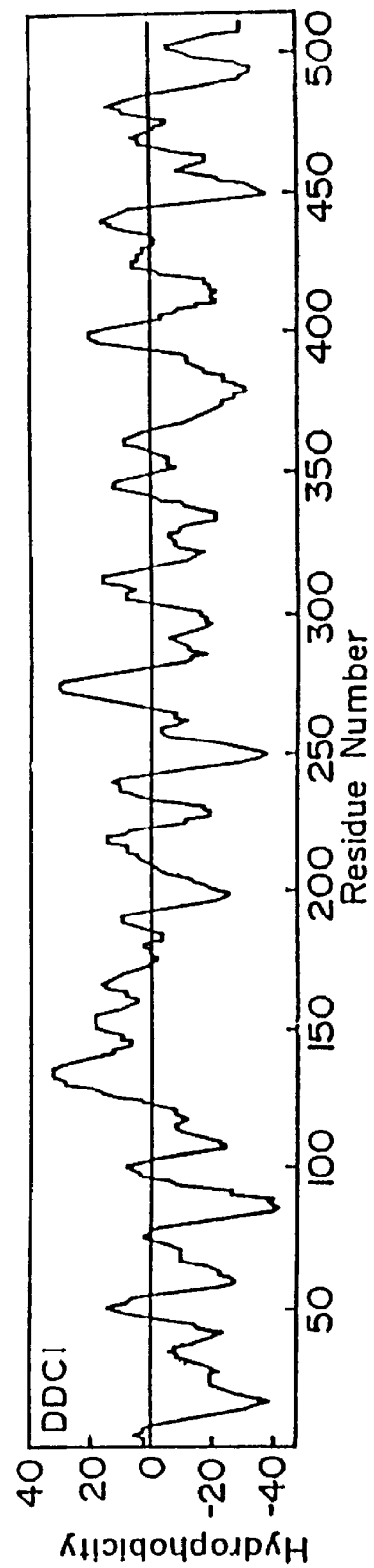

Total poly(A)$^+$ RNAs (1 µg) from six day old *C. roseus* seedlings and from young leaves of mature plants were run on an agarose/formaldehyde gel and were transferred to nitrocellulose paper. Hybridization was performed with [$^{32}$P]-labelled pTDC5 insert (sp. act. 1.2×10$^8$ cpm/µG). When total poly(A)$^+$ RNA isolated from six day old seedlings was probed with a 1.6 kb cDNA fragment isolated from pTDC5, a 1.8 kb mRNA was detected (FIG. 5, lane 1). Young leaves from the mature plant also contained a 1.8 kb mRNA (FIG. 5, lane 2). A fainter signal corresponding to a transcript of 3.2 kb was also present in both the lanes. This signal could be a precursor form of the TDC mRNA or an unrelated transcript having some sequence similarity to TDC.

h. Determination of homology between *C. roseus* TDC and opium poppy TDC

Figure 6A:
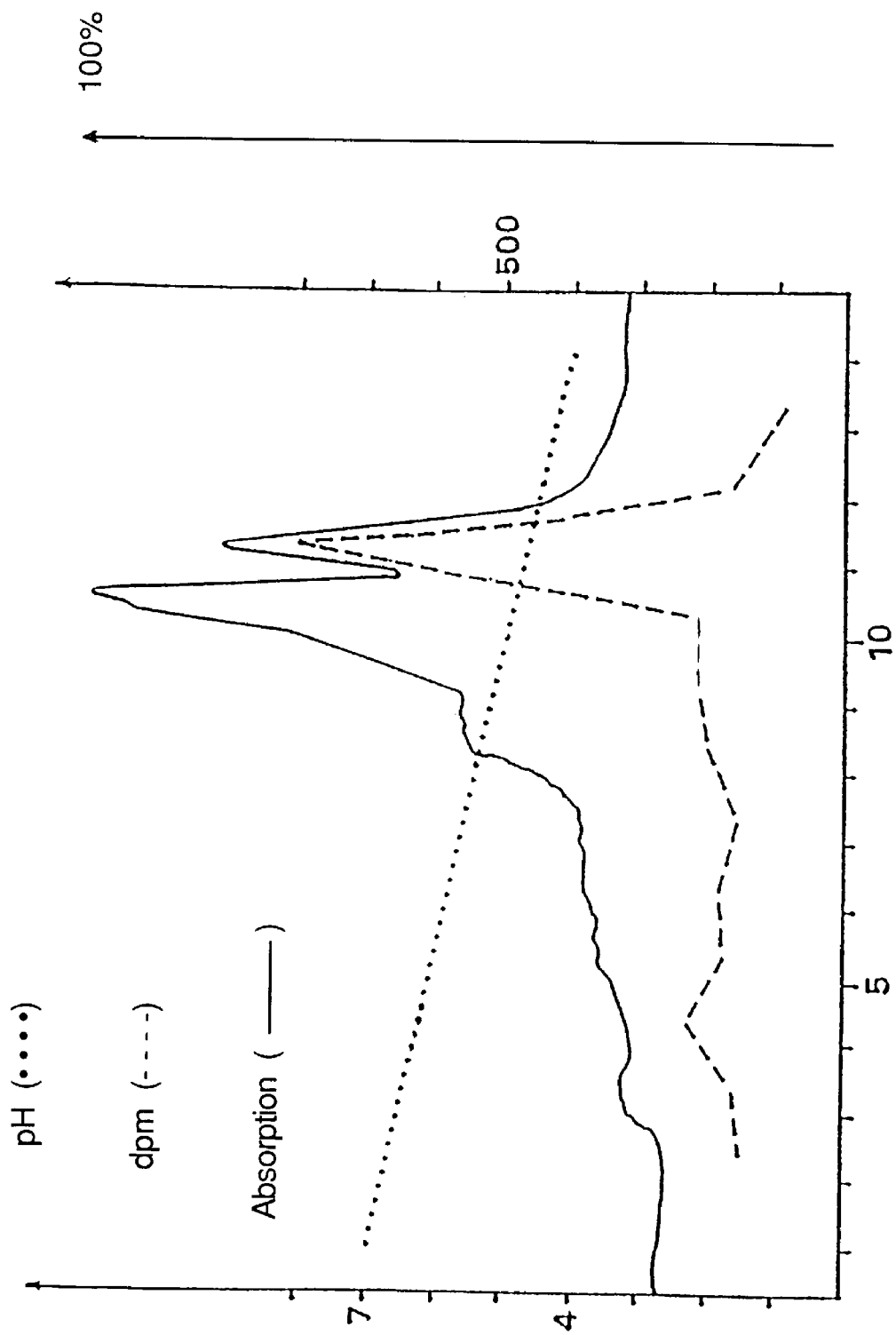
FIG. 6a represents the tyrosine decarboxylase enzymatic activity of protein fractions isolated from opium poppy.

A protein extract from opium poppy was partially purified by chromatofocussing on a Mono P high performance chromatofocussing column and the fractionated proteins were assayed for tyrosine decarboxylase enzyme activity. FIG. 6*a* shows the tyrosine decarboxylase enzymatic activity of protein fractions isolated from opium poppy. It can be seen from FIG. 1*a* that decarboxylase activity was found in fractions 10 to 12, with the majority of enzymatic activity restricted to fraction 11.

Figure 6B:
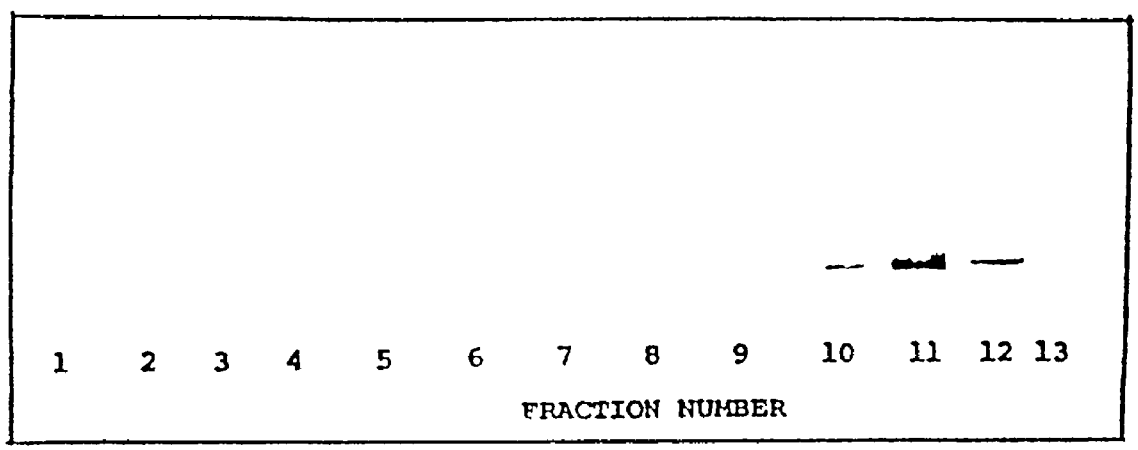
FIG. 6b represents an immunoblot of various opium poppy protein fractions.

Antibodies against tryptophan decarboxylase from *C. roseus* were used in an immunoassay of the protein fractions from opium poppy. The proteins from each of the opium poppy fractions were submitted to SDS-PAGE followed by transfer and binding of separated proteins to nitrocellulose membranes. The blotted proteins were then treated with the anti-TDC antibodies from *C. roseus*. An immunoblot of the various opium poppy protein fractions is shown in FIG. 6*b*.

The results from the immunoblot data provided in FIG. 1*b* show that fraction 11 contains an antigen with a Mr of 50,000, which cross-reacts with anti-TDC antibody from *C. roseus*.

i. Transformation of canola plants with a TDC encoding gene from *C. roseus*

A single cDNA encoding the enzyme tryptophan decarboxylase (TDC) from *C. roseus* was placed under transcriptional control of the cauliflower mosaic virus (CaMV) 35S promoter. The resulting chimaeric gene was inserted into the binary Ti plasmid vector pBI121, after deletion of the β-glucuronidase (GUS) gene. The plasmid vector pBI121 was constructed by replacement of the β-glucoronidase gene between the XbaI and SstI sites in the CaMV 35S-Nos terminator cassette of pBI121 (Clonetech) with a 2 kb XbaI–XhoI fragment from pBSKS+ (Stratagene) containing the full length tryptophan decarboxylase cDNA clone, pTDC5. The XhoI site of the fragment was linked to the SstI site using the oligonucleotide adapter TCGAGGAGCT. The construct was mobilized into the disarmed *Agrobacterium tumefaciens* strain LBA 4404 by the triparental mating procedure as described in (1986) Plant Mol. Biol. 7, 357, and used to transform canola (Brassica napus cv. Westar) plants as described in (1987) Plant Cell Reports 6, 221.

This canola cultivar produces both allyl glucosinolates and indole glucosinolates, which are derived from methionine and tryptophan, respectively. Transgenic plants, selected on kanamycin containing media, were allowed to flower and to set seed, and kanamycin resistant seedlings were used for subsequent experiments. Eighty-five putative transformed plants were obtained. Further Northern blot, Western blot, enzymatic and chemical studies revealed that 11 plants actually expressed TDC activity.

Seven independent TDC expressing transgenic canola lines were studied. In FIG. 7, the relationship between the level of tryptophan decarboxylase (TDC) activity, the accumulation of tryptamine and indole glucosinolates in different transgenic canola lines is shown. To analyze indole glucosinolates, plant materials were collected, divided into 3 parts of 1 gram fresh weight each and frozen in liquid nitrogen for analysis of TDC enzyme activity, tryptamine and glucosinolate content. Tryptamine was extracted and analyzed according to procedures described previously. Content of tryptamine (FIG. 7a), TDC activities (FIG. 7b), TDC mRNA (FIG. 7c) and indole glucosinolates (FIG. 7d) in young fully expanded leaves (solid bars) of different transgenic canola plants were compared to controls (wild-type plants and those transformed with the E. coli β-glucoronidase gene GUS 1 and GUS 2.

For mRNA measures, total RNA was extracted, processed for slot blot analysis (30 μg total RNA/slot), hybridized with $^{32}$P-labelled TDC probe (1600 bp EcoR1 fragment) and hybridizing RNA was detected by autoradiography as described in T. Maniatis, E. F. Frisch, J. Sambrook in Molecular Cloning, a laboratory manual, (1989) Cold Spring Harbor Laboratory, Cold Spring Harbor, N.Y. Relative amounts of RNA hybridizing to the labelled probe were quantified by scanning laser densitometry.

As for the indole glucosinolates, frozen plant materials were pulverized and extracted with boiling 100% methanol and re-extracted with boiling 70% methanol. After removal of the volatile solvent in vacuo, the sample was stored at −20° C. until required. Canola seed samples (30 seeds, ca. 100 mg) were ground and extracted twice with boiling 70% methanol and stored at −20° C. Prior to analysis, extracts were thawed, applied to a microcolumn of DEAE-Sephadex A25, treated with the enzyme sulphatase type H1 (Sigma) and eluted. These desulphated samples and standard desulphoglucosinolates were analyzed by HPLC as described by A. Quinsac, D. Ribailler in J. Assoc. Off. Anal. Chem. 74, 932 (1991).

The analyzed plants were 5 weeks old and had not yet flowered. They were shown to accumulate tryptamine (FIG. 7a), the immediate decarboxylation product of the TDC reaction. The concentration of tryptamine which accumulated in each transgenic plant, was correlated with both TDC specific activity (FIG. 7b) and relative TDC mRNA levels (FIG. 7c). In comparison, non-transformed control plants and those transformed with the β-glucuronidase gene expressed no TDC activity (the background activities observed are artefacts of the assay), and accumulated neither tryptamine nor TDC mRNA (FIG. 7a–c). The GUS controls also showed that the results obtained with TDC expressing plants are not an artefact of transformation.

The content of seed indole glucosinolates (FIG. 7e) and allyl glucosinolates (FIG. 7f) in transgenic canola plants is also shown compared to the same controls. Each measurement (mean±SD) represents results from three separate plants for each control and each transgenic line. The background activities observed in controls (B), are artefacts of the assay procedure and do not represent a TDC activity.

The redirection of tryptophan into tryptamine by expression of a heterologous TDC activity in canola resulted in a reduction of indole glucosinolate levels by more than 70% in leaves of all seven transgenic lines (FIG. 7d). In contrast, the levels of allyl glucosinolates remained unaltered (data not shown). Seeds of the transgenic line St004, which has the lowest TDC activity, accumulates 50% of the indole glucosinolates of control plants. Seeds of line St 062, with the highest TDC activity, accumulates only 3% of the indole glucosinolates found in control plants. In contrast, the allyl glucosinolates in seeds from all transgenic lines remained essentially unaltered (FIG. 7f). Analysis of mature seeds produced from each transgenic line demonstrated conclusively that redirecting tryptophan results in seeds containing much lower levels of indole glucosinolate (FIG. 7e).

More detailed analyses of transgenic line St 062 clearly showed the relationship between TDC activity and the lower indole glucosinolate levels accumulating in different plant parts. FIGS. 8a–8h show the analysis of tryptophan decarboxylase overexpressing canola line St 062 (hatched bars), compared to non-transformed wild-type control plants (solid bars). Levels of indole glucosinolates (FIG. 8a), allyl glucosinolates (FIG. 8b), tryptamine (FIG. 8c) and tryptophan decarboxylase (FIG. 8d) in extracts of 7-day-old seedlings, 14-day-old seedlings, young leaves before flowering (preflowering leaves), open flowers, leaves after flowering (post flowering leaves), green developing seeds and mature seeds are shown. The structures of glucosinolates found in Brassica napus cv. Westar are indole glucosinolates (FIG. 8e) and allyl glucosinolates (FIG. 8f). The structure of tryptamine is in FIG. 8g and the reaction catalyzed by tryptophan decarboxylase is in FIG. 8h. Results are given as the mean±SD from three separate plants for the wild-type control and for line St-062. The background activities observed in the wild-type control (FIG. 8d) are artefacts of the assay procedure and do not represent a TDC activity.

Protein extracts from 7-day-old seedlings, young leaves of pre-flowering plants and fully opened flowers expressed 6-fold higher levels of TDC than in wild-type control plants, while those from 14-day old roots, leaves of post-flowering plants and green developing seeds contained 3-fold higher TDC activities than background values (FIG. 8d). With the exception of mature seeds in which few active enzymes are found, the TDC-specific activity of each plant organ correlates with the quantity of tryptamine accumulated (FIG. 8c) decline of indole glucosinolate levels. This variable expression of TDC activity in all plant organs reflects the activities normally observed with genes placed behind the CaMV 35S-promoter.

The total indole glucosinolates accumulating in mature seeds of line ST 062 is 0.2±0.45 μmol/gram fresh weight of seed, compared with 6±1 μmol/gram fresh weight of untransformed seed (FIG. 8a). In contrast, seeds of line St 062 accumulate similar levels of allyl glucosinolates (16±2 μmol/gram fresh weight of seed) as untransformed seeds (13±3 μmol/gram fresh weight of seed (FIG. 8b).

Seeds of the transgenic canola plants produced above have been deposited at the American Type Culture Collection, 12301 Parklawn Drive, Rockville Md. 20852, U.S.A., under accession number 75501.

We claim:

1. A DNA fragment comprising an isolated and purified DNA sequence encoding a plant tryptophan decarboxylase, wherein the plant decarboxylase has the DNA sequence corresponding to nucleotides 69 to 1572 of the sequence designated TDC in FIG. 3.

2. A DNA fragment according to claim 1, wherein said DNA sequence encoding a plant decarboxylase is synthetically produced to correspond substantially to said isolated and purified DNA sequence and wherein the nucleotide sequence of said synthetic DNA sequence is determined on the basis of codon degeneracy.

3. A DNA construct comprising 5' to 3':
a promoter effective in the cells of a host;
a protein coding region not natively associated with the promoter, the protein coding region encoding a plant tryptophan decarboxylase protein and having the nucleotide sequence of nucleotides 69–1572 of the sequence designated TDC in FIG. 3;
a transcriptional terminator sequence,
the DNA construct being effective to express the protein coding region in the host.

4. A DNA construct as claimed in claim 3 wherein the promoter is effective in plant cells.

5. A bacterial cell comprising the DNA construct of claim 3.

6. A plant cell comprising in its genome the DNA construct of claim 3.

* * * * *